(12) United States Patent
Binette et al.

(10) Patent No.: US 7,824,701 B2
(45) Date of Patent: Nov. 2, 2010

(54) BIOCOMPATIBLE SCAFFOLD FOR LIGAMENT OR TENDON REPAIR

(75) Inventors: Francois Binette, Weymouth, MA (US); Julia Hwang, Watertown, MA (US); Mark Zimmerman, East Brunswick, NJ (US); Mora Carolynne Melican, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 658 days.

(21) Appl. No.: 10/374,754

(22) Filed: Feb. 25, 2003

(65) Prior Publication Data

US 2004/0078077 A1 Apr. 22, 2004

Related U.S. Application Data

(60) Provisional application No. 60/420,093, filed on Oct. 18, 2002, provisional application No. 60/419,539, filed on Oct. 18, 2002.

(51) Int. Cl.
A61F 2/00 (2006.01)

(52) U.S. Cl. ....................................... 424/423

(58) Field of Classification Search ........................ None
See application file for complete search history.

(56) References Cited

U.S. PATENT DOCUMENTS

| | | | |
|---|---|---|---|
| 206,200 A | 7/1878 | Stewart |
| 224,226 A | 2/1880 | Rind |
| 259,260 A | 6/1882 | Baeyer et al. |
| 3,272,204 A | 9/1966 | Artandi |
| 3,739,402 A | 6/1973 | Cooley et al. |
| 3,812,017 A | 5/1974 | Santangelo et al. |
| 3,857,932 A | 12/1974 | Shepard et al. |
| 4,045,418 A | 8/1977 | Sinclair |
| 4,057,537 A | 11/1977 | Sinclair |
| 4,105,034 A | 8/1978 | Shalaby et al. |
| 4,130,639 A | 12/1978 | Shalaby et al. |
| 4,130,689 A | 12/1978 | Costa, Jr. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,344,193 A | 8/1982 | Kenny |
| 4,520,821 A | 6/1985 | Schmidt et al. |
| 4,553,272 A | 11/1985 | Mears |
| 4,597,766 A | 7/1986 | Hilal et al. |
| 4,609,551 A | 9/1986 | Caplan et al. |
| 4,728,329 A | 3/1988 | Mansat et al. |
| 4,801,299 A | 1/1989 | Brendel et al. |
| 4,837,285 A | 6/1989 | Berg et al. |
| 4,902,508 A | 2/1990 | Badylak et al. |
| 4,946,377 A | 8/1990 | Kovach |
| 5,007,934 A | 4/1991 | Stone |
| 5,041,138 A | 8/1991 | Vacanti et al. |
| 5,053,050 A | 10/1991 | Itay |
| 5,061,281 A | 10/1991 | Mares et al. |
| 5,078,744 A * | 1/1992 | Chvapil ........................ 606/86 |
| 5,108,989 A | 4/1992 | Amento et al. |
| 5,147,400 A | 9/1992 | Kaplan et al. |
| 5,176,708 A | 1/1993 | Frey et al. |
| 5,206,023 A | 4/1993 | Hunziker |
| 5,258,028 A | 11/1993 | Ersek et al. |
| 5,263,984 A | 11/1993 | Li et al. |
| 5,306,311 A | 4/1994 | Stone et al. |
| 5,326,357 A | 7/1994 | Kandel |
| 5,366,756 A | 11/1994 | Chesterfield et al. |
| 5,425,766 A | 6/1995 | Bowald |
| 5,443,950 A | 8/1995 | Naughton et al. |
| 5,445,833 A | 8/1995 | Badylak et al. |
| 5,455,041 A | 10/1995 | Genco et al. |
| 5,464,929 A | 11/1995 | Bezwada et al. |
| 5,468,253 A | 11/1995 | Bezwada et al. |
| 5,480,827 A | 1/1996 | Guillemin et al. |
| 5,487,897 A | 1/1996 | Polson et al. |
| 5,514,181 A | 5/1996 | Light et al. |
| 5,514,378 A | 5/1996 | Mikos et al. |
| 5,571,189 A | 11/1996 | Kuslich |
| 5,577,517 A | 11/1996 | Bonutti |
| 5,589,176 A | 12/1996 | Seare, Jr. |
| 5,595,751 A | 1/1997 | Bezwada et al. |

(Continued)

FOREIGN PATENT DOCUMENTS

AU 717552 3/1998

(Continued)

OTHER PUBLICATIONS

The term "derive" Merriam-Webster Online Dictionary, see at the web- http://www.m-w.com, p. 1.*
Murray M.M. et al. The migration of cells from the ruptured human anterior cruciate ligament into collagen-glycosaminoglycan regeneration templates in vitro, Biomaterials, 2001, 22: 2393-2402, entire document.*
Bonisch, M., et al. "Septumredonstrucktion mit PDS-Folie" HNO 47: 1999 pp. 546-550.
Eckersberger, M.D., Franz, "Circumferential tracheal replacement with costal cartilage", The Journal of Thoracic and Cardiovascular Surgery, 1987;94: pp. 175-180.
Matsuo, M.D., Kiyoshi et al., "Semiquantitative Correction of Posttraumatic Enophthalmos with Sliced Cartilage Grafts" Plastic and Reconstructive Surgery, vol. 83, No. 3, Postraumatic Enophthalmos, pp. 429-437.

(Continued)

*Primary Examiner*—Jon P Weber
*Assistant Examiner*—Satyendra K Singh

(57) ABSTRACT

A biocompatible ligament repair implant or scaffold device is provided for use in repairing a variety of ligament tissue injuries. The repair procedures may be conducted with ligament repair implants that contain a biological component that assists in healing or tissue repair. The biocompatible ligament repair implants include a biocompatible scaffold and particles of viable tissue derived from ligament tissue or tendon tissue, such that the tissue and the scaffold become associated. The particles of living tissue contain one or more viable cells that can migrate from the tissue and populate the scaffold.

33 Claims, 10 Drawing Sheets

U.S. PATENT DOCUMENTS

| | | |
|---|---|---|
| 5,597,579 A | 1/1997 | Bezwada et al. |
| 5,607,687 A | 3/1997 | Bezwada et al. |
| 5,612,028 A | 3/1997 | Sackier et al. |
| 5,618,552 A | 4/1997 | Bezwada et al. |
| 5,620,698 A | 4/1997 | Bezwada et al. |
| 5,624,463 A | 4/1997 | Stone et al. |
| 5,632,745 A | 5/1997 | Schwartz |
| 5,645,850 A | 7/1997 | Bezwada et al. |
| 5,648,088 A | 7/1997 | Bezwada et al. |
| 5,654,135 A | 8/1997 | Tinois et al. |
| 5,656,492 A | 8/1997 | Glowacki et al. |
| 5,677,355 A | 10/1997 | Shalaby et al. |
| 5,681,353 A | 10/1997 | Li et al. |
| 5,697,976 A | 12/1997 | Chesterfield et al. |
| 5,698,213 A | 12/1997 | Jamiolkowski et al. |
| 5,700,583 A | 12/1997 | Jamiolkowski et al. |
| 5,709,854 A | 1/1998 | Griffith-Cima et al. |
| 5,720,969 A | 2/1998 | Gentile et al. |
| 5,723,331 A | 3/1998 | Tubo et al. |
| 5,735,903 A | 4/1998 | Li et al. |
| 5,736,372 A | 4/1998 | Vacanti et al. |
| 5,755,791 A | 5/1998 | Whitson et al. |
| 5,759,190 A | 6/1998 | Vibe-Hansen et al. |
| 5,766,631 A | 6/1998 | Arnold |
| 5,769,899 A | 6/1998 | Schwartz et al. |
| 5,786,217 A | 7/1998 | Tubo et al. |
| 5,830,493 A | 11/1998 | Yokota et al. |
| 5,837,235 A | 11/1998 | Mueller et al. |
| 5,842,477 A | 12/1998 | Naughton et al. |
| 5,855,608 A | 1/1999 | Brekke et al. |
| 5,859,150 A | 1/1999 | Jamiolkowski et al. |
| 5,891,558 A | 4/1999 | Bell et al. |
| 5,902,741 A | 5/1999 | Purchio et al. |
| 5,904,716 A | 5/1999 | Gendler |
| 5,904,717 A | 5/1999 | Brekke et al. |
| 5,914,121 A | 6/1999 | Robey et al. |
| 5,922,025 A | 7/1999 | Hubbard |
| 5,964,805 A | 10/1999 | Stone |
| 5,968,096 A | 10/1999 | Whitson et al. |
| 5,980,889 A | 11/1999 | Butler et al. |
| 5,989,269 A | 11/1999 | Vibe-Hanen et al. |
| 5,990,194 A | 11/1999 | Dunn et al. |
| 5,990,378 A | 11/1999 | Ellis |
| 6,001,352 A | 12/1999 | Boyan et al. |
| 6,001,394 A | 12/1999 | Daculsi et al. |
| 6,005,161 A | 12/1999 | Brekke et al. |
| 6,027,742 A | 2/2000 | Lee et al. |
| 6,042,610 A | 3/2000 | Li et al. |
| 6,054,122 A | 4/2000 | MacPhee et al. |
| 6,077,989 A | 6/2000 | Kandel et al. |
| 6,080,579 A | 6/2000 | Hanley, Jr. et al. |
| 6,096,532 A | 8/2000 | Armstrong et al. |
| 6,103,255 A | 8/2000 | Levene et al. |
| 6,110,209 A | 8/2000 | Stone |
| 6,110,212 A | 8/2000 | Gregory |
| 6,117,166 A | 9/2000 | Winston et al. |
| 6,120,514 A | 9/2000 | Vibe-Hanen et al. |
| 6,121,042 A | 9/2000 | Peterson et al. |
| 6,123,727 A * | 9/2000 | Vacanti et al. ............... 424/422 |
| 6,132,463 A | 10/2000 | Lee et al. |
| 6,132,468 A | 10/2000 | Mansmann |
| 6,139,578 A | 10/2000 | Lee et al. |
| 6,140,039 A | 10/2000 | Naughton et al. |
| 6,143,293 A | 11/2000 | Weiss et al. |
| 6,153,292 A | 11/2000 | Bell et al. |
| 6,156,068 A | 12/2000 | Walter et al. |
| 6,176,880 B1 | 1/2001 | Plouhar et al. |
| 6,179,840 B1 | 1/2001 | Bowman |
| 6,179,872 B1 | 1/2001 | Bell et al. |
| 6,180,007 B1 | 1/2001 | Gentile et al. |
| 6,183,737 B1 | 2/2001 | Zaleske et al. |
| 6,187,053 B1 | 2/2001 | Minuth |
| 6,187,329 B1 | 2/2001 | Agrawal et al. |
| 6,197,061 B1 | 3/2001 | Masuda et al. |
| 6,197,325 B1 | 3/2001 | MacPhee et al. |
| 6,200,606 B1 | 3/2001 | Peterson et al. |
| 6,214,045 B1 | 4/2001 | Corbitt, Jr. et al. |
| 6,214,055 B1 | 4/2001 | Simionescu et al. |
| 6,242,247 B1 | 6/2001 | Rieser et al. |
| 6,251,673 B1 | 6/2001 | Winkler |
| 6,277,151 B1 | 8/2001 | Lee et al. |
| 6,283,980 B1 | 9/2001 | Vibe-Hansen et al. |
| 6,287,340 B1 | 9/2001 | Altman et al. |
| 6,291,240 B1 | 9/2001 | Mansbridge et al. |
| 6,306,177 B1 | 10/2001 | Felt et al. |
| 6,306,424 B1 | 10/2001 | Vyakarnam et al. |
| 6,316,692 B1 | 11/2001 | Readhead et al. |
| 6,319,712 B1 | 11/2001 | Meenen et al. |
| 6,331,312 B1 | 12/2001 | Lee et al. |
| 6,333,029 B1 | 12/2001 | Vyakarnam et al. |
| 6,365,149 B2 | 4/2002 | Vyakarnam et al. |
| 6,378,527 B1 | 4/2002 | Hungerford et al. |
| 6,378,572 B1 | 4/2002 | Neubauer et al. |
| 6,379,367 B1 | 4/2002 | Vibe-Hansen et al. |
| 6,464,729 B1 | 10/2002 | Kandel |
| 6,485,723 B1 | 11/2002 | Badylak et al. |
| 6,489,165 B2 | 12/2002 | Bhatnagar et al. |
| 6,511,958 B1 | 1/2003 | Atkinson et al. |
| 6,530,956 B1 | 3/2003 | Mansmann |
| 6,534,084 B1 * | 3/2003 | Vyakarnam et al. ......... 424/443 |
| 6,541,024 B1 | 4/2003 | Kadiyala et al. |
| 6,551,355 B1 | 4/2003 | Lewandrowski et al. |
| 6,569,172 B2 | 5/2003 | Asculai et al. |
| 6,592,588 B1 | 7/2003 | Bobic et al. |
| 6,599,323 B2 | 7/2003 | Melican et al. |
| 6,605,294 B2 | 8/2003 | Sawhney |
| 6,626,950 B2 | 9/2003 | Brown et al. |
| 6,727,224 B1 | 4/2004 | Zhang et al. |
| 6,773,458 B1 | 8/2004 | Brauker et al. |
| 6,783,712 B2 | 8/2004 | Slivka et al. |
| 6,840,962 B1 * | 1/2005 | Vacanti et al. ........... 623/23.76 |
| 6,852,330 B2 | 2/2005 | Bowman et al. |
| 6,866,681 B2 | 3/2005 | Laboureau et al. |
| 6,884,428 B2 | 4/2005 | Binette et al. |
| 6,886,568 B2 | 5/2005 | Frondoza et al. |
| 6,886,569 B2 | 5/2005 | Chervitz et al. |
| 7,208,177 B2 | 4/2007 | Geistlich et al. |
| 7,262,020 B2 | 8/2007 | Hellerstein |
| 2001/0014475 A1 | 8/2001 | Frondoza et al. |
| 2001/0016353 A1 | 8/2001 | Janas et al. |
| 2001/0016772 A1 | 8/2001 | Lee et al. |
| 2001/0023373 A1 | 9/2001 | Plouhar et al. |
| 2001/0038848 A1 | 11/2001 | Donda et al. |
| 2001/0039453 A1 | 11/2001 | Gresser et al. |
| 2001/0051834 A1 | 12/2001 | Frondoza et al. |
| 2001/0053353 A1 | 12/2001 | Griffith et al. |
| 2001/0053839 A1 | 12/2001 | Noishiki et al. |
| 2002/0006428 A1 | 1/2002 | Mahmood et al. |
| 2002/0009477 A1 | 1/2002 | Mahmood et al. |
| 2002/0009805 A1 | 1/2002 | Nevo et al. |
| 2002/0009806 A1 | 1/2002 | Hicks, Jr. |
| 2002/0013627 A1 | 1/2002 | Geistlich et al. |
| 2002/0015719 A1 | 2/2002 | Kellner et al. |
| 2002/0022883 A1 | 2/2002 | Burg |
| 2002/0022884 A1 | 2/2002 | Mansmann |
| 2002/0028192 A1 | 3/2002 | Dimitrijevich et al. |
| 2002/0029055 A1 | 3/2002 | Bonutti |
| 2002/0062151 A1 | 5/2002 | Altman et al. |
| 2002/0082631 A1 | 6/2002 | Bonutti |
| 2002/0083479 A1 | 6/2002 | Winston et al. |
| 2002/0091403 A1 | 7/2002 | Bonutti |
| 2002/0091406 A1 | 7/2002 | Bonutti |
| 2002/0099401 A1 | 7/2002 | Bonutti |
| 2002/0099448 A1 | 7/2002 | Hiles et al. |

| | | | |
|---|---|---|---|
| 2002/0107570 A1 | 8/2002 | Sybert et al. |
| 2002/0119177 A1 | 8/2002 | Bowman et al. |
| 2002/0127265 A1 | 9/2002 | Bowman et al. |
| 2002/0133229 A1 | 9/2002 | Laurencin et al. |
| 2002/0133235 A1 | 9/2002 | Hungerford et al. |
| 2002/0150604 A1 | 10/2002 | Yi et al. |
| 2002/0151975 A1 | 10/2002 | Farr et al. |
| 2002/0173558 A1 | 11/2002 | Williams et al. |
| 2002/0176893 A1 | 11/2002 | Wironen et al. |
| 2002/0177224 A1 | 11/2002 | Madry et al. |
| 2003/0003153 A1 | 1/2003 | Asculai et al. |
| 2003/0004578 A1 | 1/2003 | Brown et al. |
| 2003/0012805 A1 | 1/2003 | Chen et al. |
| 2003/0023316 A1 | 1/2003 | Brown et al. |
| 2003/0026787 A1 | 2/2003 | Fearnot et al. |
| 2003/0027332 A1 | 2/2003 | Lafrance et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0050709 A1 | 3/2003 | Noth et al. |
| 2003/0064917 A1 | 4/2003 | Crawford et al. |
| 2003/0075822 A1 | 4/2003 | Slivka et al. |
| 2003/0077311 A1 | 4/2003 | Vyakarnam et al. |
| 2003/0078617 A1 | 4/2003 | Schwartz et al. |
| 2004/0024457 A1 | 2/2004 | Boyce et al. |
| 2004/0059416 A1 | 3/2004 | Murray et al. |
| 2004/0078077 A1 | 4/2004 | Binette et al. |
| 2004/0078090 A1 | 4/2004 | Binette et al. |
| 2004/0219182 A1 | 11/2004 | Gomes et al. |
| 2004/0236424 A1 | 11/2004 | Berez et al. |
| 2004/0267362 A1 | 12/2004 | Hwang et al. |
| 2005/0002915 A1 | 1/2005 | Atala et al. |
| 2005/0038520 A1 | 2/2005 | Binette et al. |
| 2005/0113937 A1 | 5/2005 | Binette et al. |
| 2005/0125077 A1 | 6/2005 | Harmon et al. |
| 2005/0147645 A1 | 7/2005 | Budny |
| 2005/0234549 A1 | 10/2005 | Kladakis et al. |
| 2006/0084930 A1 | 4/2006 | Dhanaraj et al. |
| 2006/0204439 A1 | 9/2006 | Hellerstein |
| 2006/0223177 A1 | 10/2006 | Harris et al. |
| 2006/0280768 A1 | 12/2006 | Hwang et al. |
| 2006/0293760 A1 | 12/2006 | DeDeyne |
| 2007/0036767 A1 | 2/2007 | Mistry et al. |
| 2007/0250177 A1 | 10/2007 | Bilbo |
| 2008/0039955 A1 | 2/2008 | Hunziker |

FOREIGN PATENT DOCUMENTS

| | | |
|---|---|---|
| CA | 2247158 | 8/1997 |
| DE | 198 12 195 | 9/1999 |
| EP | 0145492 | 6/1985 |
| EP | 0 274 898 | 7/1988 |
| EP | 0464163 | 1/1992 |
| EP | 0 562 864 | 9/1993 |
| EP | 0 955 024 | 11/1999 |
| EP | 1 027 897 | 8/2000 |
| EP | 1 064 958 | 1/2001 |
| EP | 1 167 517 | 1/2002 |
| EP | 1 216 718 | 6/2002 |
| EP | 1 348 451 | 10/2003 |
| EP | 1 410 811 | 4/2004 |
| EP | 1405649 | 4/2004 |
| EP | 1 506 790 | 2/2005 |
| EP | 1537839 | 6/2005 |
| EP | 1604622 | 12/2005 |
| FR | 2688690 A1 | 9/1993 |
| GB | 1008193 A | 10/1965 |
| JP | 2143945 U | 12/1990 |
| JP | 19900227442 A | 4/1992 |
| JP | 19900256824 A | 5/1992 |
| JP | 19910261753 A | 7/1993 |
| JP | 19920094329 A | 11/1993 |
| JP | 10234844 A | 9/1998 |
| JP | 19980129048 A | 11/1999 |
| JP | 19980319783 A | 5/2000 |
| JP | 2001129073 A | 5/2001 |
| JP | 2003320008 A | 11/2003 |
| JP | 2004008437 A | 1/2004 |
| JP | 20020165345 A | 1/2004 |
| RU | 2187261 | 8/2002 |
| SU | 1535542 | 1/1990 |
| WO | WO 86/00533 | 1/1986 |
| WO | 9206179 A1 | 4/1992 |
| WO | 9302718 A1 | 2/1993 |
| WO | 9311805 A1 | 6/1993 |
| WO | WO 95/33821 | 12/1995 |
| WO | 9608277 A1 | 3/1996 |
| WO | WO 97/30662 | 8/1997 |
| WO | WO 97/46665 | 12/1997 |
| WO | WO 98/48860 | 11/1998 |
| WO | 9853768 A1 | 12/1998 |
| WO | WO 99/16381 | 4/1999 |
| WO | 9939724 A1 | 8/1999 |
| WO | WO 99/47097 | 9/1999 |
| WO | 0015248 | 3/2000 |
| WO | 0016381 | 3/2000 |
| WO | 0069355 A1 | 11/2000 |
| WO | 0072782 A1 | 12/2000 |
| WO | WO 00/74741 | 12/2000 |
| WO | WO 01/15753 | 3/2001 |
| WO | 0134065 A1 | 5/2001 |
| WO | WO 01/85226 | 11/2001 |
| WO | 0205750 | 1/2002 |
| WO | 0205750 A2 | 1/2002 |
| WO | 2002000272 A2 | 1/2002 |
| WO | 02074356 | 9/2002 |
| WO | 02096268 A2 | 12/2002 |
| WO | 03007789 | 1/2003 |
| WO | WO 03/017826 | 3/2003 |
| WO | 03043674 A1 | 5/2003 |
| WO | 2004012782 | 2/2004 |

OTHER PUBLICATIONS

Megumi, M.D., Yoshikazu, "Augmentation Rhinoplasty with Soft Tissue and Cartilage" Aesthetic Plastic Surgery, 1988, pp. 89-933.

Papadopulos, M.D., Angel, "Compound Implant to Projedt the Nasal Tip" Aesthetic Plastic Surgery, 1987, pp. 181-185.

Partial European Search Report, for EP 04 25 7515, mailed May 9, 2005.

Powers, Dennis L. et al., "A cartilagenous graft as an adjunct to finger joint implant arthroplasty" Journal of Biomedical Materials Research, vol. 19, 1985 pp. 509-518.

Rohrbach, Jens Martin et al., "Biological Corneal Replacement—Alternative to Keratoplasty and Keratoprosthesis? A Pilot Study with Heterologous Hyaline Cartilage in the Rabbit Model", Klin Monatsbl Augenheilkd 207, 1995; pp. 191-196.

Trenite, M.D., G.J. Nolst et al., "Reimplantation of autologous septal cartilage in the growing nasal septum", Rhinology, 25, 1987, pp. 225-236.

Albrecht et al., Closure of Osteochondral Lesions Using Chondral Fragments and Fibrin Adhesives, Arch. Orthop. Trauma Surg. (1983) 101: 213-217.

Thomas F. Deuel and Nan Zhang, "Growth Factors" in Principles of Tissue Engineering, Second Edition, Academic Press, 2000, pp. 129-141.

Sally R. Frenkel, Ph.D. and Paul E. Di Cesare, M.D., "Degradation and Repair of Articular Cartilage" in Frontiers in Bioscience, 4th ed., pp. 671-685, Oct. 15, 1999, pp. 1-32.

Keith J. Gooch et al., "Mechanical Forces and Growth Factors Utilized in Tissue Engineering" in Frontier in Tissue Engineering, Pergamon, 1998, Chapter II.3, pp. 61-82.

John A. Koski, M.D. et al., "Meniscal Injury and Repair", Orthopedic Clinics of North American, vol. 31, No. 3, Jul. 2000, pp. 419-435.

John A. Koski, M.D. et al., "Tissue-Engineered Ligament—Cells, Matrix, and Growth Factors" in Tissue Engineering in Orthopedic Surgery, vol. 31, No. 3, Jul. 2000, pp. 437-452.

Clemente Ibarra, M.D. et al. "Tissue-Engineered Meniscus—Cells and Matrix", in Tissue Engineering in Orthopedic Surgery, vol. 31, No. 3, Jul. 2000, pp. 411-418.

Stone, K. et al. "Meniscal Regeneration with Copolymeric Collagen Scaffolds" *American Journal of Sports Medicine*, 20(2):104-111 (1992).

Murray, M., et al. "The Migration of Cells from the Ruptured Human Anterior Cruciate Ligament into Collagen-Glycosaminoglycan Regeneration Templates in Vitro" *Biomaterials* 22:2393-2402 (2001).

(Abstract Only) Caterson EJ., et al. "Three-Dimensional Cartilage Formation by Bone Marrow-Derived Cells Seeded in Polylactide/Alginate Amalgam" *J Biomed Mater Res*, 57(3):394-403(2001).

(Abstract Only) Grigolo, B., et al. "Transplantation of Chondrocytes Seeded on a Hyaluronan Derivative (hyaff-11) into Cartilage Defects in Rabbits" *Biomaterials* 22(17):2417-2424 (2001).

(Abstract Only) van Susante JLC, et al. "Linkage of Chondroitin-sulfate to Type I Collagen Scaffolds Stimulates the Bioactivity of Seeded Chondrocytes in Vitro", *Biomaterials*, 22(17):2359-2369 (2001).

(Abstract Only) Hutmacher DW., "Scaffold Design and Fabrication Technologies for Engineering Tissues—State of the Art and Future Prospectives", *J Biomater Sci Polym Ed*, 12(1):107-124 (2001).

(Abstract Only) Hutmacher DW., "Scaffolds in Tissue Engineering Bone and Cartilage", *Biomaterials*, 21(24):2529-2543 (2000).

(Abstract Only) Schreiber RE., et al. "A Method for Tissue Engineering of cartilage by Cell Seeding on Bioresorbable Scaffolds" *Ann NY Acad Sci*, 875:394-404 (1999).

(Abstract Only) Radice, M. "Hyaluronan-Based Biopolymers as delivery vehicles for Bone-Marrow-Derived Mesenchymal Progenitors", *J Biomed Mater Res*, 50(2) :101-9 (2000).

Albrecht et al., "Closure of Joint Cartilage Defects by Means of Cartilage Fragments and Fibrin Adhesive," *Fortschr. Med.* 101(37): 1650-52 (1983).

European Search Report, for EP 03 25 6522, mailed Feb. 24, 2004.

Rossi, et.al., "Embryonic Purkinje Cells Grafted on the Surface of the Cerebellar Cortex Integrate in the Adult Unlesioned Cerebellum," *EP J. Neuroscience* 4:589-93 (1992).

Sampath, T. K., et al. "In Vitro Transformation of Mesenchymal Cells Derived From Embryonic Muscle Into Cartilage in Response to Extracellular Matrix Components of Bone," *Proceedings of the National Academy of Science of the USA*, 81(1): 3419-3423 (Jun. 1984).

Boland et. al., J. Macromol. Sci.-Pure Appl. Chem., 2001, A38(12), p. 1231-1243).

Buschmann et al., J. Orthop. Res. 1992; 10:745-752.

De Groot, J.H. et al., "Meniscal tissue regeneration in porous 50/50 copoly(l-lactide/epsilon-caprolactone) implants" Biomaterials, vol. 18, No. 8, 1997, pp. 613-622.

De Groot, J.H. et al., "Use of porous polyurethanes for meniscal reconstruction and meniscal prostheses" Biomaterials, vol. 17, No. 2, 1996, pp. 163-173.

European Search Report, for EP Application No. 07252617.1, mailed Nov. 2, 2007.

Microcellular Foams via Phase Separation, J. Vac. Sci. Technolol., A.T. Young, vol. 4(3), May/Jun. 1986.

Solov'ev et al., "Functional Activity of Hepatocytes in Liver Fragments in Vitro as a Function if Fragment Size and Duration of Culturing" Bull Exp Biol Med. Jun. 2000;129(6):595-7.

Spaans et al. "Solvent-free fabrication of micro-porous polyurethane amide and polyurethane-urea scaffolds for repair and replacement of the knee joint meniscus" Journal of Biomaterials, vol. 21, No. 23, 2000, pp. 2453-2460.

Australian Examiner's first report on patent application No. 2006200194, mailed Feb. 4, 2008.

Tienen T. G. et al., "A porous polymer scaffold for meniscal lesion repair—A study in dogs" Biomaterials, vol. 24, No. 14, 2003, pp. 2541-2548.

Tozum et al., J Canadian Dental Assoc. Nov. 2003 69(10):664-664h.

Kemnitzer and Kohn, in the Handbook of Biodegradable Polymers, edited by Domb, et. al., Hardwood Academic Press, pp. 251-272 (1997).

Journal of Biomaterials Research, vol. 22, pp. 993-1009, 1988 by Cohn and Younes.

Polymer Preprints (ACS Division of Polymer Chemistry), vol. 30(1), p. 498, 1989 by Cohn.

Allcock in the Encyclopedia of Polymer Science, vol. 13, pp. 31-41, Wiley Intersciences, John Wiley & Sons, 1988.

Vandorpe, et al in the Handbook of Biodegradable Polymers, edited by Domb, et al., Hardwood Academic Press, pp. 161-182 (1997).

Dialog English language abstract for DE 19812195.

Ikada, Yoshito, Handbook of Fiber Science and Technology, Edited by Menachem Lewin, Jack Preston, vol. III, Part B, Chapter 8, pp. 253, 289-295, Published by M. Dekker, 1983.

Kurashina, K. et al. "Osteogenesis in muscle with composite graft of hydroxyapatite and autogenous calvarial periosteum: a preliminary report" Biomaterials (1995) vol. 16, No. 2, pp. 119-123.

Nioshiki Y., "A new trend in hybrid artificial organs" J. Artificial Organs, 1999, vol. 2: pp. 93-96.

www.btc-bti.com/applications/cryogenicstorage.htm, 6 pgs, printed Jan. 11, 2010.

www.bio-medicine.org/medicine-technology-1/New-Study-Shows-Cloning-From-Dried-Cells-Now-Possible-2988-1/, 2 pgs, printed Jan. 11, 2010.

Chen G., Ushida T. and Tateishi T., "A hybrid network of synthetic polymer mesh and collagen sponge," Chem. Commun., 2000, pp. 1505-1506.

European Search Report for EP 08075114.2, mailed May 12, 2010.

Heller: 'Handbook of Biodegradable Polymers,' 1997, Hardwood Academic Press, pp. 99-118.

* cited by examiner

H/E

SO

MMAB

→ Old Bone Fragments
→ New Bone Formation
→ New Cartilage

| ⟶ | Old Bone Fragments |
|---|---|
| ⟶ | New Bone Formation |
| ⟶ | New Cartilage |

Minced Cartilage

Cartilage 2mm

Cartilage 3mm

BIOCOMPATIBLE SCAFFOLD FOR LIGAMENT OR TENDON REPAIR

CROSS REFERENCE TO RELATED APPLICATIONS

This application claims priority to U.S. Provisional Patent Application No. 60/419,539 filed on Oct. 18, 2002 and entitled "Biocompatible Scaffold for Ligament or Tendon Repair," and to U.S. Provisional Patent Application No. 60/420,093 filed on Oct. 18, 2002 and entitled "Biocompatible Scaffold With Tissue Fragments."

FIELD OF THE INVENTION

The present invention relates to biocompatible tissue implant devices for use in the repair of tissue injuries, as well as methods for making and using such biocompatible tissue implant devices.

BACKGROUND OF THE INVENTION

Injuries to soft tissue, such as cartilage, skin, muscle, bone, tendon and ligament, where the tissue has been injured or traumatized frequently require surgical intervention to repair the damage and facilitate healing. Such surgical repairs can include suturing or otherwise repairing the damaged tissue with known medical devices, augmenting the damaged tissue with other tissue, using an implant, a graft or any combination of these techniques.

One common tissue injury involves damage to cartilage, which is a non-vascular, resilient, flexible connective tissue. Cartilage typically acts as a "shock-absorber" at articulating joints, but some types of cartilage provide support to tubular structures, such as for example, the larynx, air passages, and the ears. In general, cartilage tissue is comprised of cartilage cells, known as chondrocytes, located in an extracellular matrix, which contains collagen, a structural scaffold, and aggrecan, a space-filling proteoglycan. Several types of cartilage can be found in the body, including hyaline cartilage, fibrocartilage and elastic cartilage. Hyaline cartilage can appear in the body as distinct pieces, or alternatively, this type of cartilage can be found fused to the articular ends of bones. Hyaline cartilage is generally found in the body as articular cartilage, costal cartilage, and temporary cartilage (i.e., cartilage that is ultimately converted to bone through the process of ossification). Fibrocartilage is a transitional tissue that is typically located between tendon and bone, bone and bone, and/or hyaline cartilage and hyaline cartilage. Elastic cartilage, which contains elastic fibers distributed throughout the extracellular matrix, is typically found in the epiglottis, the ears and the nose.

One common example of hyaline cartilage injury is a traumatic focal articular cartilage defect to the knee. A strong impact to the joint can result in the complete or partial removal of a cartilage fragment of various size and shape. Damaged articular cartilage can severely restrict joint function, cause debilitating pain and may result in long term chronic diseases such as osteoarthritis, which gradually destroys the cartilage and underlying bone of the joint. Injuries to the articular cartilage tissue will not heal spontaneously and require surgical intervention if symptomatic. The current modality of treatment consists of lavage, removal of partially or completely unattached tissue fragments. In addition, the surgeon will often use a variety of methods such as abrasion, drilling or microfractures, to induce bleeding into the cartilage defect and formation of a clot. It is believed that the cells coming from the marrow will form a scar-like tissue called fibrocartilage that can provide temporary relief to some symptoms. Unfortunately, the fibrocartilage tissue does not have the same mechanical properties as hyaline cartilage and degrades faster over time as a consequence of wear. Patients typically have to undergo repeated surgical procedures which can lead to the complete deterioration of the cartilage surface. More recently, experimental approaches involving the implantation of autologous chondrocytes have been used with increasing frequency. The process involves the harvest of a small biopsy of articular cartilage in a first surgical procedure, which is then transported to a laboratory specialized in cell culture for amplification. The tissue biopsy is treated with enzymes that will release the chondrocyte cells from the matrix, and the isolated cells will be grown for a period of 3 to 4 weeks using standard tissue culture techniques. Once the cell population has reached a target number, the cells are sent back to the surgeon for implantation during a second surgical procedure. This manual labor-intense process is extremely costly and time consuming. Although, the clinical data suggest long term benefit for the patient, the prohibitive cost of the procedure combined with the traumatic impact of two surgical procedures to the knee, has hampered adoption of this technique.

One common example of cartilage injury is damage to the menisci of a knee joint. There are two menisci of the knee joint, a medial and a lateral meniscus. Each meniscus is a biconcave, fibrocartilage tissue that is interposed between the femur and tibia of the leg. In addition to the menisci of the knee joint, meniscal cartilage can also be found in the acromioclavicular joint, i.e., the joint between the clavicle and the acromion of the scapula, in the sternoclavicular joint, i.e., the joint between the clavicle and the sternum, and in the temporomandibular joint, i.e., the joint of the lower jaw. The primary functions of meniscal cartilage are to bear loads, to absorb shock and to stabilize a joint. If not treated properly, an injury to the meniscus, such as a "bucket-handle tear" in the knee joint, may lead to the development of osteoarthritis. Current conventional treatment modalities for damaged meniscal cartilage include the removal and/or surgical repair of the damaged cartilage.

Another common form of tissue injury involves damage to the ligaments and/or tendons. Ligaments and tendons are cords or bands of fibrous tissue that contains soft collagenous tissue. Ligaments connect bone to bone, while tendons connect muscle to bone. Tendons are fibrous cords or bands of variable length that have considerable strength but are virtually devoid of elasticity. Ligaments, in contrast, are generally pliant and flexible, to allow the ligament tissue to have freedom of movement, and simultaneously strong and inextensible, to prevent the ligament tissue from readily yielding under applied force. Ligaments and tendons are comprised of fascicles, which contain the basic fibril of the ligament or tendon, as well as the cells that produce the ligament or tendon, known as fibroblasts. The fascicles of the tendon are generally comprised of very densely arranged collagenous fibers, parallel rows of elongated fibroblasts, and a proteoglycan matrix. The fascicles of ligaments also contain a proteoglycan matrix, fibroblasts and collagen fibrils, but the fibrils found in ligament tissue are generally less dense and less structured than the fibrils found in tendon tissue.

One example of a common ligament injury is a torn anterior cruciate ligament (ACL), which is one of four major ligaments of the knee. The primary function of the ACL is to constrain anterior translation, rotary laxity and hyperextension. The lack of an ACL causes instability of the knee joint and leads to degenerative changes in the knee such as osteoarthritis. The most common repair technique is to remove and discard the ruptured ACL and reconstruct a new ACL using autologous bone-patellar, tendon-bone or hamstring tendons. Although this technique has shown long-term clinical efficacy, there is morbidity associated with the harvest site of the tissue graft. Synthetic prosthetic devices have been clinically evaluated in the past with little long-term success. The advantages of a synthetic implant are that the patient does not suffer from the donor site morbidity that is associated with autograft procedures, and that patients having a synthetic implant are able to undergo faster rehabilitation of the knee. These synthetic devices were composed of non-resorbable materials and were designed to be permanent prosthetic implants. A number of problems were found during the clinical trials of these implants, such as for example, synovitis, bone tunnel enlargement, wear debris, and elongation and rupture of the devices. For this reason, autograft reconstruction is still the widely accepted solution for repairing a ruptured ACL.

A common tendon injury is a damaged or torn rotator cuff, which is the portion of the shoulder joint that facilitates circular motion of the humerus bone relative to the scapula. The most common injury associated with the rotator cuff is a strain or tear to the supraspinatus tendon. This tear can occur at the insertion site of the supraspinatus tendon, where the tendon attaches to the humerus, thereby partially or fully releasing the tendon (depending upon the severity of the injury) from the bone. Additionally, the strain or tear can occur within the tendon itself. Treatment for a strained tendon usually involves rest and reduced use of the tendon. However, depending upon the severity of the injury, a torn tendon may require surgical intervention, such as for example, in the case of a full tear of the supraspinatus tendon from the humerus. In the case of severe tendon damage, surgical intervention can involve the repair and/or reattachment of torn tissue, which typically requires a healing and recovery period.

There is a continuing need in this art for novel surgical techniques for the surgical treatment of damaged tissue (e.g., cartilage, meniscal cartilage, ligaments, tendons and skin) that can effect a more reliable repair of tissue and can facilitate the healing of damaged tissue. Various surgical implants are known and have been used in surgical procedures to help achieve these benefits. For example, it is known to use various devices and techniques for creating implants having isolated cells loaded onto a delivery vehicle. Such cell-seeded implants are used in an in vitro method of making and/or repairing cartilage by growing cartilaginous structures that consist of chondrocytes seeded onto biodegradable, biocompatible fibrous polymeric matrices. Such methods require the initial isolation of chondrocytes from cartilaginous tissue prior to the chondrocytes being seeded onto the polymeric matrices. Other techniques for repairing damaged tissue employ implants having stem or progenitor cells that are used to produce the desired tissue. For example, it is known to use stem or progenitor cells, such as the cells within fatty tissue, muscle, or bone marrow, to regenerate bone and/or cartilage in a patient. The stem cells are removed from the patient and placed in an environment favorable to cartilage formation, thereby inducing the fatty tissue cells to proliferate and to create a different type of cell, such as for example, cartilage cells.

There continues to exist a need in this art for novel devices and methods for making and/or repairing damaged tissue and for hastening the healing of the damaged tissue.

SUMMARY OF THE INVENTION

This invention relates to biocompatible tissue implants for use in treating tissue, and the methods for making and using these devices. For example, the tissue implants can be used for the repair and/or regeneration of diseased or damaged tissue. Further, the tissue implants can be used for tissue bulking, cosmetic treatments, therapeutic treatments, tissue augmentation, and tissue repair. The implants include a biocompatible scaffold that is associated with a suspension containing at least one minced tissue fragment. The biocompatible tissue implants can also include an additional biological agent and/or an optional retaining element placed over the suspension of minced tissue.

The invention also relates to a method of preparing such biocompatible tissue implants. The implants are made by providing at least one biocompatible scaffold and a sample of minced tissue, processing the tissue sample to create a suspension of viable tissue having at least one minced tissue fragment, and depositing the tissue sample upon the biocompatible scaffold. In one embodiment, the method of producing these implants can include the further step of incubating the tissue-laden scaffold in a suitable environment for a duration and under conditions that are sufficient to effectively allow cells within the tissue sample to populate the scaffold.

The invention is also directed to a kit to assist in the preparation of the tissue implants of the present invention. The kits of the present invention include a sterile container which houses at least one biocompatible scaffold, a harvesting tool for collecting a tissue sample from a subject, and one or more reagents for sustaining the viability of the tissue sample. The kit can also include a processing tool for mincing the tissue into tissue particles, or alternatively, the harvesting tool can be adapted to collect the tissue sample and to process the sample into finely divided tissue particles. The kit can, optionally, also include a delivery device for transferring the scaffold from the sterile container to a subject for implantation.

The invention also relates to methods of treating tissue using the biocompatible tissue implants of the present invention. Tissue treatment according to these methods can be performed by providing a biocompatible scaffold and a sample of minced tissue, depositing the tissue sample upon the biocompatible scaffold, and placing the tissue-laden scaffold in a desired position relative to the tissue to be treated. In one embodiment, tissue repair can be achieved by providing a biocompatible scaffold and a sample of minced tissue, depositing the tissue sample in a desired position relative to the tissue injury, and placing the biocompatible scaffold over the tissue. In another embodiment, the method of producing these implants can include the further step of incubating the tissue-laden scaffold in a suitable environment for a duration and under conditions that are effective to allow cells within the tissue sample to populate the scaffold. In yet another embodiment, the methods of treating tissue can also include the additional step of affixing the scaffold in a desired position relative to the tissue to be treated, such as, for example, by fastening the tissue-laden scaffold in place.

The present invention is also directed to methods for measuring the effect(s) of a substance on living tissue. According to this aspect of the invention, the bioimplantable tissue implants of the present invention can be used to create tissue constructs that can be contacted with a test substance so that the effects of the substance on living tissue can be observed and measured. Thus, the bioimplantable tissue constructs of the present invention can be used as a biological screening assay to measure the effects of a test substance on living tissue by examining the effect on various biological responses, such as for example, the effect on cell migration, cell proliferation and differentiation and maintenance of cell phenotype.

In embodiments in which the implant is used for tissue repair, the tissue repair implant can be used to treat a variety of injuries, such as for example, injuries occurring within the musculoskeletal system, such as rotator cuff injuries, ACL ruptures, or meniscal tears, as well as injuries occurring in other connective tissues, such as skin and cartilage. Furthermore, such implants can be used in other orthopaedic surgical procedures, such as hand and foot surgery, to repair tissues such as ligaments, nerves, and tendons.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1A:
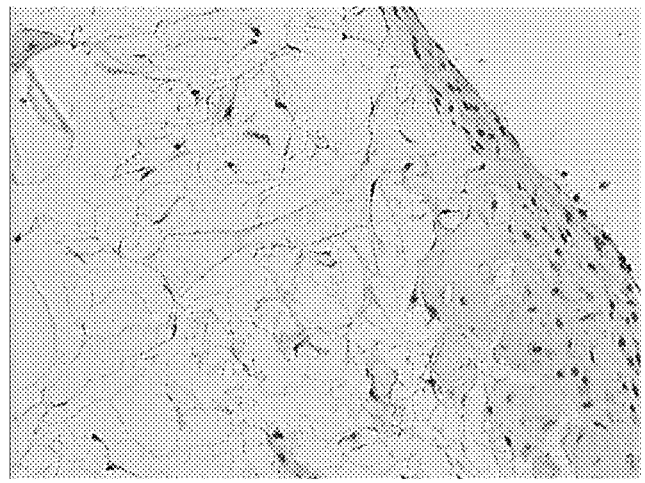
FIG. 1A is photomicrograph that demonstrates that cells in a cartilage tissue sample migrate extensively into a polymer scaffold.

The biocompatible tissue implants of the present invention are used in the treatment of various types of tissue for various purposes. For example, the implants can be used for the repair and/or regeneration of diseased or damaged tissue, or they can be used for tissue bulking, tissue augmentation, cosmetic treatments, therapeutic treatments, and for tissue sealing. The tissue implants include a biocompatible scaffold and a suspension of minced tissue having at least one minced tissue fragment, wherein the minced tissue suspension is associated with the scaffold. The minced tissue in the suspension of the present invention includes at least one viable cell that can migrate from the tissue fragment and onto the scaffold.

Although the implants are sometimes referred to herein as "tissue repair implants" and the methods of using the implants are sometimes characterized as tissue repair techniques, it is understood that the implants can be used for a variety of tissue treatments, including but not limited to tissue repair, tissue bulking, cosmetic treatments, therapeutic treatments, tissue augmentation, and tissue sealing.

The biocompatible tissue implant of the present invention includes a biocompatible scaffold having at least a portion in contact with the minced tissue suspension. The minced tissue suspension can be disposed on the outer surface of the scaffold, on an inner region of the scaffold, and any combination thereof, or alternatively, the entire scaffold can be in contact with the minced tissue suspension. The scaffold can be formed using virtually any material or delivery vehicle that is biocompatible, bioimplantable, easily sterilized and that has sufficient structural integrity and physical and/or mechanical properties to effectively provide for ease of handling in an operating room environment and to permit it to accept and retain sutures or other fasteners without substantially tearing. Alternatively, the scaffold could be in the form of an injectable gel that would set in place at the defect site. Sufficient strength and physical properties are developed in the scaffold through the selection of materials used to form the scaffold, and the manufacturing process. Preferably, the scaffold is also pliable so as to allow the scaffold to adjust to the dimensions of the target site of implantation. In some embodiments, the scaffold can be a bioresorbable or bioabsorbable material.

In one embodiment of the present invention, the scaffold can be formed from a biocompatible polymer. A variety of biocompatible polymers can be used to make the biocompatible tissue implants or scaffold devices according to the present invention. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring. In embodiments where the scaffold includes at least one synthetic polymer, suitable biocompatible synthetic polymers can include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof. Suitable synthetic polymers for use in the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-,L- and meso lactide); glycolide (including glycolic acid); $\epsilon$-caprolactone; p-dioxanone (1,4-dioxan-2-one); trimethylene carbonate (1,3-dioxan-2-one); alkyl derivatives of trimethylene carbonate; $\delta$-valerolactone; $\beta$-butyrolactone; $\gamma$-butyrolactone; $\epsilon$-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; $\alpha,\alpha$ diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30 (1), page 498, 1989 by Cohn (e.g., PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al., Hardwood Academic Press, pp. 161-182 (1997). Polyanhydrides include those derived from diacids of the form HOOC—$C_6H_4$—O—$(CH_2)_m$—O—$C_6H_4$—COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al., Hardwood Academic Press, pp. 99-118 (1997).

As used herein, the term "glycolide" is understood to include polyglycolic acid. Further, the term "lactide" is understood to include L-lactide, D-lactide, blends thereof, and lactic acid polymers and copolymers.

Elastomeric copolymers are also particularly useful in the present invention. Suitable elastomeric polymers include those with an inherent viscosity in the range of about 1.2 dL/g to 4 dL/g, more preferably about 1.2 dL/g to 2 dL/g and most preferably about 1.4 dL/g to 2 dL/g as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In the preferred embodiments of this invention, the elastomer exhibits a percent elongation greater than about 200 percent and preferably greater than about 500 percent. In addition to these elongation and modulus properties, suitable elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers that can be used in the present invention include, but are not limited to, elastomeric copolymers of $\epsilon$-caprolactone and glycolide (including polyglycolic acid) with a mole ratio of $\epsilon$-caprolactone to glycolide of from about 35:65 to about 65:35, more preferably from 45:55 to 35:65; elastomeric copolymers of $\epsilon$-caprolactone and lactide (including L-lactide, D-lactide, blends thereof, and lactic acid polymers and copolymers) where the mole ratio of $\epsilon$-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of $\epsilon$-caprolactone and p-dioxanone where the mole ratio of $\epsilon$-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable biocompatible elastomers are described in U.S. Pat. Nos. 4,045,418; 4,057,537 and 5,468,253.

In one embodiment, the elastomer is a copolymer of 35:65 $\epsilon$-caprolactone and glycolide, formed in a dioxane solvent and including a polydioxanone mesh. In another embodiment, the elastomer is a copolymer of 40:60 $\epsilon$-caprolactone and lactide with a polydioxanone mesh. In yet another embodiment, the elastomer is a 50:50 blend of a 35:65 copolymer of $\epsilon$-caprolactone and glycolide and 40:60 copolymer of $\epsilon$-caprolactone and lactide. The polydioxanone mesh may be in the form of a one layer thick two-dimensional mesh or a multi-layer thick three-dimensional mesh.

The scaffold of the present invention can, optionally, be formed from a bioresorbable or bioabsorbable material that has the ability to resorb in a timely fashion in the body environment. The differences in the absorption time under in vivo conditions can also be the basis for combining two different copolymers when forming the scaffolds of the present invention. For example, a copolymer of 35:65 ε-caprolactone and glycolide (a relatively fast absorbing polymer) can be blended with 40:60 ε-caprolactone and L-lactide copolymer (a relatively slow absorbing polymer) to form a biocompatible scaffold. Depending upon the processing technique used, the two constituents can be either randomly interconnected bicontinuous phases, or the constituents could have a gradient-like architecture in the form of a laminate type composite with a well integrated interface between the two constituent layers. The microstructure of these scaffolds can be optimized to regenerate or repair the desired anatomical features of the tissue that is being regrown.

In one embodiment, it is desirable to use polymer blends to form scaffolds which transition from one composition to another composition in a gradient-like architecture. Scaffolds having this gradient-like architecture are particularly advantageous in tissue engineering applications to repair or regenerate the structure of naturally occurring tissue such as cartilage (articular, meniscal, septal, tracheal, auricular, costal, etc.), tendon, ligament, nerve, esophagus, skin, bone, and vascular tissue. For example, by blending an elastomer of ε-caprolactone-co-glycolide with ε-caprolactone-co-lactide (e.g., with a mole ratio of about 5:95) a scaffold may be formed that transitions from a softer spongy material to a stiffer more rigid material, for example, in a manner similar to the transition from cartilage to bone. Clearly, one of ordinary skill in the art will appreciate that other polymer blends may be used for similar gradient effects, or to provide different gradients (e.g., different absorption profiles, stress response profiles, or different degrees of elasticity). For example, such design features can establish a concentration gradient for the suspension of minced tissue associated with the scaffolds of the present invention, such that a higher concentration of the tissue fragments is present in one region of the implant (e.g., an interior portion) than in another region (e.g., outer portions).

The biocompatible scaffold of the tissue repair implant of the present invention can also include a reinforcing material comprised of any absorbable or non-absorbable textile having, for example, woven, knitted, warped knitted (i.e., lace-like), non-woven, and braided structures. In one embodiment, the reinforcing material has a mesh-like structure. In any of the above structures, mechanical properties of the material can be altered by changing the density or texture of the material, the type of knit or weave of the material, the thickness of the material, or by embedding particles in the material. The mechanical properties of the material may also be altered by creating sites within the mesh where the fibers are physically bonded with each other or physically bonded with another agent, such as, for example, an adhesive or a polymer. The fibers used to make the reinforcing component can be monofilaments, yarns, threads, braids, or bundles of fibers. These fibers can be made of any biocompatible material including bioabsorbable materials such as polylactic acid (PLA), polyglycolic acid (PGA), polycaprolactone (PCL), polydioxanone (PDO), trimethylene carbonate (TMC), copolymers or blends thereof. These fibers can also be made from any biocompatible materials based on natural polymers including silk and collagen-based materials. These fibers can also be made of any biocompatible fiber that is nonresorbable, such as, for example, polyethylene, polyethylene terephthalate, poly(tetrafluoroethylene), polycarbonate, polypropylene and poly(vinyl alcohol). In one embodiment, the fibers are formed from 95:5 copolymer of lactide and glycolide.

In another embodiment, the fibers that form the reinforcing material can be made of a bioabsorbable glass. Bioglass, a silicate containing calcium phosphate glass, or calcium phosphate glass with varying amounts of solid particles added to control resorption time are examples of materials that could be spun into glass fibers and used for the reinforcing material. Suitable solid particles that may be added include iron, magnesium, sodium, potassium, and combinations thereof.

The biocompatible scaffolds as well as the reinforcing material may also be formed from a thin, perforation-containing elastomeric sheet with pores or perforations to allow tissue ingrowth. Such a sheet could be made of blends or copolymers of polylactic acid (PLA), polyglycolic acid (PGA), polycaprolactone (PCL), and polydioxanone (PDO).

In one embodiment, filaments that form the biocompatible scaffolds or the reinforcing material may be co-extruded to produce a filament with a sheath/core construction. Such filaments are comprised of a sheath of biodegradable polymer that surrounds one or more cores comprised of another biodegradable polymer. Filaments with a fast-absorbing sheath surrounding a slower-absorbing core may be desirable in instances where extended support is necessary for tissue ingrowth.

One of ordinary skill in the art will appreciate that one or more layers of the reinforcing material may be used to reinforce the tissue implant of the invention. In addition, biodegradable textile scaffolds, such as, for example, meshes, of the same structure and chemistry or different structures and chemistries can be overlaid on top of one another to fabricate biocompatible tissue implants with superior mechanical strength.

In embodiments where the scaffold includes at least one natural polymer, suitable examples of natural polymers include, but are not limited to, fibrin-based materials, collagen-based materials, hyaluronic acid-based materials, glycoprotein-based materials, cellulose-based materials, silks and combinations thereof. By way of nonlimiting example, the biocompatible scaffold can be constructed from a collagen-based small intestine submucosa.

In another embodiment of the present invention, the biocompatible scaffold can be formed from a biocompatible ceramic material. Suitable biocompatible ceramic materials include, for example, hydroxyapatite, α-tricalcium phosphate, β-tricalcium phosphate, bioactive glass, calcium phosphate, calcium sulfate, calcium carbonate, xenogeneic and allogeneic bone material and combinations thereof. Suitable bioactive glass materials for use in the present invention include silicates containing calcium phosphate glass, or calcium phosphate glass with varying amounts of solid particles added to control resorption time. Suitable compounds that may be incorporated into the calcium phosphate bioactive glass include, but are not limited to, magnesium oxide, sodium oxide, potassium oxide, and combinations thereof.

In yet another embodiment of the tissue implants of the present invention, the scaffold can be formed using tissue grafts, such as may be obtained from autogeneic tissue, allogeneic tissue and xenogeneic tissue. By way of non-limiting example, tissues such as skin, cartilage, ligament, tendon, periosteum, perichondrium, synovium, fascia, mesenter and sinew can be used as tissue grafts to form the biocompatible scaffold. In some embodiments where an allogeneic tissue is used, tissue from a fetus or newborns can be used to avoid the immunogenicity associated with some adult tissues.

In another embodiment, the scaffold could be in the form of an injectable gel that would set in place at the defect site. The gel can be a biological or synthetic hydrogel, including alginate, cross-linked alginate, hyaluronic acid, collagen gel, fibrin glue, fibrin clot, poly(N-isopropylacrylamide), agarose, chitin, chitosan, cellulose, polysaccharides, poly(oxyalkylene), a copolymer of poly(ethylene oxide)-poly(propylene oxide), poly(vinyl alcohol), polyacrylate, platelet rich plasma (PRP) clot, platelet poor plasma (PPP) clot, Matrigel, or blends thereof.

In still yet another embodiment of the tissue implants, the scaffold can be formed from a polymeric foam component having pores with an open cell pore structure. The pore size can vary, but preferably, the pores are sized to allow tissue ingrowth. More preferably, the pore size is in the range of about 50 to 1000 microns, and even more preferably, in the range of about 50 to 500 microns. The polymeric foam component can, optionally, contain a reinforcing component, such as for example, the textiles disclosed above. In some embodiments where the polymeric foam component contains a reinforcing component, the foam component can be integrated with the reinforcing component such that the pores of the foam component penetrate the mesh of the reinforcing component and interlock with the reinforcing component.

The foam component of the tissue implant may be formed as a foam by a variety of techniques well known to those having ordinary skill in the art. For example, the polymeric starting materials may be foamed by lyophilization, supercritical solvent foaming (i.e., as described in EP 464,163), gas injection extrusion, gas injection molding or casting with an extractable material (e.g., salts, sugar or similar suitable materials).

In one embodiment, the foam component of the engineered tissue repair implant devices of the present invention may be made by a polymer-solvent phase separation technique, such as lyophilization. Generally, however, a polymer solution can be separated into two phases by any one of the four techniques: (a) thermally induced gelation/crystallization; (b) non-solvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous structure with a density less than the bulk polymer and pores in the micrometer ranges. See Microcellular Foams Via Phase Separation, J. Vac. Sci. Technol., A. T. Young, Vol. 4 (3), May/June 1986.

The steps involved in the preparation of these foams include choosing the right solvents for the polymers to be lyophilized and preparing a homogeneous solution. Next, the polymer solution is subjected to a freezing and vacuum drying cycle. The freezing step phase separates the polymer solution and vacuum drying step removes the solvent by sublimation and/or drying, leaving a porous polymer structure or an interconnected open cell porous foam.

Suitable solvents that may be used in the preparation of the foam component include, but are not limited to, formic acid, ethyl formate, acetic acid, hexafluoroisopropanol (HFIP), cyclic ethers (e.g., tetrahydrofuran (THF), dimethylene fluoride (DMF), and polydioxanone (PDO)), acetone, acetates of C2 to C5 alcohols (e.g., ethyl acetate and t-butylacetate), glyme (e.g., monoglyme, ethyl glyme, diglyme, ethyl diglyme, triglyme, butyl diglyme and tetraglyme), methylethyl ketone, dipropyleneglycol methyl ether, lactones (e.g., γ-valerolactone, δ-valerolactone, β-butyrolactone, γ-butyrolactone), 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, a preferred solvent is 1,4-dioxane. A homogeneous solution of the polymer in the solvent is prepared using standard techniques.

The applicable polymer concentration or amount of solvent that may be utilized will vary with each system. Generally, the amount of polymer in the solution can vary from about 0.5% to about 90% and, preferably, will vary from about 0.5% to about 30% by weight, depending on factors such as the solubility of the polymer in a given solvent and the final properties desired in the foam.

In one embodiment, solids may be added to the polymer-solvent system to modify the composition of the resulting foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting tissue implant, thus causing compositional changes in all such regions. For example, concentration of solids in selected locations can be accomplished by adding metallic solids to a solution placed in a mold made of a magnetic material (or vice versa).

A variety of types of solids can be added to the polymer-solvent system. Preferably, the solids are of a type that will not react with the polymer or the solvent. Generally, the added solids have an average diameter of less than about 1.0 mm and preferably will have an average diameter of about 50 to about 500 microns. Preferably, the solids are present in an amount such that they will constitute from about 1 to about 50 volume percent of the total volume of the particle and polymer-solvent mixture (wherein the total volume percent equals 100 volume percent).

Exemplary solids include, but are not limited to, particles of demineralized bone, calcium phosphate particles, bioglass particles, calcium sulfate, or calcium carbonate particles for bone repair, leachable solids for pore creation and particles of bioabsorbable polymers not soluble in the solvent system that are effective as reinforcing materials or to create pores as they are absorbed, and non-bioabsorbable materials.

Suitable leachable solids include nontoxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. Such a process is described in U.S. Pat. No. 5,514,378. Preferably the foam will be dried after the leaching process is complete at low temperature and/or vacuum to minimize hydrolysis of the foam unless accelerated absorption of the foam is desired.

Suitable non-bioabsorbable materials include biocompatible metals such as stainless steel, cobalt chrome, titanium and titanium alloys, and bioinert ceramic particles (e.g., alumina, zirconia, and calcium sulfate particles). Further, the non-bioabsorbable materials may include polymers such as polyethylene, polyvinylacetate, polymethylmethacrylate, polypropylene, poly(ethylene terephthalate), silicone, polyethylene oxide, polyethylene glycol, polyurethanes, polyvinyl alcohol, natural polymers (e.g., cellulose particles, chitin, and keratin), and fluorinated polymers and copolymers (e.g., polyvinylidene fluoride, polytetrafluoroethylene, and hexafluoropropylene).

It is also possible to add solids (e.g., barium sulfate) that will render the tissue implants radio opaque. The solids that may be added also include those that will promote tissue regeneration or regrowth, as well as those that act as buffers, reinforcing materials or porosity modifiers.

As noted above, porous, reinforced tissue repair implant devices of the present invention are made by injecting, pouring, or otherwise placing, the appropriate polymer solution into a mold set-up comprised of a mold and the reinforcing elements of the present invention. The mold set-up is cooled in an appropriate bath or on a refrigerated shelf and then lyophilized, thereby providing a reinforced scaffold. A biological component can be added either before or after the lyophilization step. In the course of forming the foam component, it is believed to be important to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogenous nucleation occurs. One of ordinary skill in the art can readily optimize the parameters without undue experimentation.

The required general processing steps include the selection of the appropriate materials from which the polymeric foam and the reinforcing components are made. If a mesh reinforcing material is used, the proper mesh density must be selected. Further, the reinforcing material must be properly aligned in the mold, the polymer solution must be added at an appropriate rate and, preferably, into a mold that is tilted at an appropriate angle to avoid the formation of air bubbles, and the polymer solution must be lyophilized.

In embodiments that utilize a mesh reinforcing material, the reinforcing mesh has to be of a certain density. That is, the openings in the mesh material must be sufficiently small to render the construct sutureable or otherwise fastenable, but not so small as to impede proper bonding between the foam and the reinforcing mesh as the foam material and the open cells and cell walls thereof penetrate the mesh openings. Without proper bonding the integrity of the layered structure is compromised leaving the construct fragile and difficult to handle. Because the density of the mesh determines the mechanical strength of the construct, the density of the mesh can vary according to the desired use for tissue repair. In addition, the type of weave used in the mesh can determine the directionality of the mechanical strength of the construct, as well as the mechanical properties of the reinforcing material, such as for example, the elasticity, stiffness, burst strength, suture retention strength and ultimate tensile strength of the construct. By way of non-limiting example, the mesh reinforcing material in a foam-based biocompatible scaffold of the present invention can be designed to be stiff in one direction, yet elastic in another, or alternatively, the mesh reinforcing material can be made isotropic.

During the lyophilization of the reinforced foam, several parameters and procedures are important to produce implants with the desired integrity and mechanical properties. Preferably, the reinforcement material is substantially flat when placed in the mold. To ensure the proper degree of flatness, the reinforcement (e.g., mesh) is pressed flat using a heated press prior to its placement within the mold. Further, in the event that reinforcing structures are not isotropic it is desirable to indicate this anisotropy by marking the construct to indicate directionality. This can be accomplished by embedding one or more indicators, such as dyed markings or dyed threads, within the woven reinforcements. The direction or orientation of the indicator will indicate to a surgeon the dimension of the implant in which physical properties are superior.

As noted above, the manner in which the polymer solution is added to the mold prior to lyophilization helps contribute to the creation of a tissue implant with adequate mechanical integrity. Assuming that a mesh reinforcing material will be used, and that it will be positioned between two thin (e.g., 0.75 mm) shims it should be positioned in a substantially flat orientation at a desired depth in the mold. The polymer solution is poured in a way that allows air bubbles to escape from between the layers of the foam component. Preferably, the mold is tilted at a desired angle and pouring is effected at a controlled rate to best prevent bubble formation. One of ordinary skill in the art will appreciate that a number of variables will control the tilt angle and pour rate. Generally, the mold should be tilted at an angle of greater than about 1 degree to avoid bubble formation. In addition, the rate of pouring should be slow enough to enable any air bubbles to escape from the mold, rather than to be trapped in the mold.

If a mesh material is used as the reinforcing component, the density of the mesh openings is an important factor in the formation of a resulting tissue implant with the desired mechanical properties. A low density, or open knitted mesh material, is preferred. One preferred material is a 90:10 copolymer of glycolide and lactide, sold under the tradename VICRYL (Ethicon, Inc., Somerville, N.J.). One exemplary low density, open knitted mesh is Knitted VICRYL VKM-M, available from Ethicon, Inc., Somerville, N.J. Other preferred materials are polydioxanone or 95:5 copolymer of lactide and glycolide.

The density or "openness" of a mesh material can be evaluated using a digital photocamera interfaced with a computer. In one evaluation, the density of the mesh was determined using a Nikon SMZ-U Zoom with a Sony digital photocamera DKC-5000 interfaced with an IBM 300PL computer. Digital images of sections of each mesh magnified to 20× were manipulated using Image-Pro Plus 4.0 software in order to determine the mesh density. Once a digital image was captured by the software, the image was thresholded such that the area accounting for the empty spaces in the mesh could be subtracted from the total area of the image. The mesh density was taken to be the percentage of the remaining digital image. Implants with the most desirable mechanical properties were found to be those with a mesh density in the range of about 12 to 80% and more preferably about 45 to 80%.

In one embodiment, the preferred scaffold for cartilage repair is a mesh reinforced foam. More preferably, the foam is reinforced with a mesh that includes polydioxanone (PDO) and the foam composition is a copolymer of 35:65 $\epsilon$-caprolactone and glycolide. For articular cartilage, the preferred structure to allow cell and tissue ingrowth is one that has an open pore structure and is sized to sufficiently allow cell migration. A suitable pore size is one in which an average diameter is in the range of about 50 to 1000 microns, and more preferably, between about 50 to 500 microns. The mesh layer has a thickness in the range of about 1 micron to 1000 microns. Preferably, the foam has a thickness in the range of about 300 microns to 2 mm, and more preferably, between about 500 microns and 1.5 mm. Preferably, the mesh layer has a mesh density in the range of about 12 to 80% and more preferably about 45 to 80%.

In another embodiment, the preferred scaffold for cartilage repair is a nonwoven structure. More preferably, the composition of the nonwoven structure are PANACRYL, a 95:5 copolymer of lactide and glycolide, VICRYL, a 90:10 copolymer of glycolide and lactide, or a blend of polydioxanone and VICRYL sold under the tradename ETHISORB (Johnson & Johnson International, Belgium). For articular cartilage, the preferred structure to allow cell and tissue ingrowth is one that has an open pore structure and is sized to sufficiently allow cell migration. A suitable pore size for the nonwoven scaffold is one in which an average diameter is in the range of about 50 to 1000 microns and more preferably between about 100 to 500 microns. The nonwoven scaffold has a thickness between about 300 microns and 2 mm, and more preferably, between about 500 microns and 1.5 mm.

In one embodiment, the preferred scaffold for meniscus repair is a mesh reinforced foam. More preferably, the foam is reinforced foam with a mesh that includes polydioxanone (PDO) and the foam composition is a copolymer of 35:65 ε-caprolactone and glycolide. The preferred structure to allow cell and tissue ingrowth is one that has an open pore structure and is sized to sufficiently allow cell migration. A suitable pore size is one in which an average diameter is in the range of about 50 to 1000 microns, and more preferably, between about 50 to 500 microns. The mesh layer has a thickness in the range of about 1 micron to 1000 microns. Preferably, the foam has a thickness in the range of about 300 microns to 2 mm, and more preferably, between about 500 microns and 1.5 mm. In this embodiment, the preferred method of use is to surround the minced cartilage tissue with this scaffold material. Preferably, the mesh layer has a mesh density in the range of about 12 to 80% and more preferably about 45 to 80%.

In one embodiment, the preferred scaffold for tendon or ligament repair is a mesh reinforced foam. More preferably, the foam is reinforced with a mesh that includes polydioxanone (PDO) and the foam composition is a copolymer of 35:65 ε-caprolactone and glycolide. The preferred structure to allow cell and tissue ingrowth is one that has an open pore structure and is sized to sufficiently allow cell migration. A suitable pore size is one in which an average diameter is in the range of about 50 to 1000 microns, and more preferably, between about 50 to 500 microns. The mesh layer has a thickness in the range of about 1 micron to 1000 microns. Preferably, the foam has a thickness in the range of about 300 microns to 2 mm, and more preferably, between about 500 microns and 1.5 mm. Preferably, the mesh layer has a mesh density in the range of about 12 to 80% and more preferably about 45 to 80%.

In another embodiment, the preferred scaffold for tendon or ligament repair is constructed from a polymer that has a slow resorption profile (e.g., at least three months, and preferably, at least six months) and high mechanical strength. More preferably, the tensile strength and elastic modulus of the scaffold must be similar to that of native ligament. The preferred tensile strength of the scaffold is between about 500N and 4000N, and more preferably, between about 1000N and 2500N. The preferred elastic modulus of the scaffold is between about 100 N/m and 300 N/m, and more preferably, between about 150 N/m and 200 N/m. The preferred structure of this scaffold is a cylindrical-shaped or elliptically-shaped scaffold or a scaffold with a high aspect ratio (i.e., ratio of length to width). Preferably, the aspect ratio is greater than 1, and more preferably it is greater than 2 and less than 100. Further, the scaffold preferably has a diameter or width in the range of about 3 mm and 12 mm, and more preferably, between about 4 mm and 10 mm. By way of non-limiting example, the scaffold for ligament repair can include a 95:5 copolymer of lactide and glycolide. In one embodiment, the scaffold for ligament repair can be formed as a composite structure including a 95:5 copolymer of lactide and glycolide and other polymers, such as for example, polylactide, polyglycolide, polydioxanone, polycaprolactone and combinations thereof. The scaffold may be formed of a woven, knit or braided material. Optionally, the polymers from which the scaffold is made can be formed as a nonwoven, textile structure, such as for example, a weave or a mesh structure, or alternatively these polymers can be formed as a foam. In another embodiment, the composite structure can include natural polymers, such as for example, collagen, fibrin, or silk. In this embodiment, the natural polymer can act as a coating to the composite structure, or alternatively, the natural polymer can be formed as a foam. The composite structure can also optionally include strips of collagen or silk to reside within the whole scaffold or just the periphery of the scaffold.

In one embodiment, the scaffold useful for ligament or tendon repair is formed of a plurality of filaments, a majority of the fibers of which are aligned in the longitudinal direction.

One of ordinary skill in the art will appreciate that the selection of a suitable material for forming the biocompatible scaffold of the present invention depends on several factors. These factors include in vivo mechanical performance; cell response to the material in terms of cell attachment, proliferation, migration and differentiation; biocompatibility; and optionally, bioabsorption (or biodegradation) kinetics. Other relevant factors include the chemical composition, spatial distribution of the constituents, the molecular weight of the polymer, and the degree of crystallinity.

In addition to the biocompatible scaffold, the tissue repair implants of the present invention further include at least one sample of viable tissue that is associated with at least a portion of the scaffold. The term "viable," as used herein, refers to a tissue sample having one or more viable cells. Virtually any type of tissue can be used to construct the tissue repair implants of the present invention. Preferably, the tissue used is selected from cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood and combinations thereof. In one embodiment useful for cartilage repair, the tissue is free of bone tissue and is selected from the group consisting of cartilage tissue, meniscal tissue, ligament tissue and tendon tissue. The tissue used to construct the tissue implant can be autogeneic tissue, allogeneic tissue, or xenogeneic tissue.

In one embodiment useful for meniscal repair, the tissue used in the tissue repair implant can be selected from the group consisting of meniscal tissue, cartilage tissue, skin, synovial tissue, periosteal tissue, pericardial tissue, fat tissue, bone marrow, blood, tendon tissue, ligament tissue, or combinations thereof. In one embodiment useful for ligament repair, the tissue used in the tissue repair implant can be selected from the group consisting of tendon tissue, ligament tissue of the same type that is to be repaired, ligament tissue of a different type than the tissue that is to be repaired, synovial tissue, periosteal tissue, fascia, skin, and combinations thereof.

The tissue can be obtained using any of a variety of conventional techniques, such as for example, by biopsy or other surgical removal. Preferably, the tissue sample is obtained under aseptic conditions. Once a sample of living tissue has been obtained, the sample can then be processed under sterile conditions to create a suspension having at least one minced, or finely divided, tissue particle. The particle size of each tissue fragment can vary, for example, the tissue size can be in the range of about 0.1 and 3 mm$^3$, in the range of about 0.5 and 1 mm³, in the range of about 1 to 2 mm³, or in the range of about 2 to 3 mm³, but preferably the tissue particle is less than 1 mm³.

Preferably, the minced tissue has at least one viable cell that can migrate from the tissue fragment onto the scaffold. More preferably, the tissue contains an effective amount of cells that can migrate from the tissue fragment and begin populating the scaffold. In an optional embodiment, the minced tissue fragments may be contacted with a matrix-digesting enzyme to facilitate cell migration out of the extracellular matrix surrounding the cells. The enzymes are used to increase the rate of cell migration out of the extracellular matrix and into the scaffold material. Suitable matrix-digesting enzymes that can be used in the present invention include, but are not limited to, collagenase, chondroitinase, trypsin, elastase, hyaluronidase, petidase, thermolysin and protease.

In one embodiment, the minced tissue particles can be formed as a suspension in which the tissue particles are associated with a physiological buffering solution. Suitable physiological buffering solutions include, but are not limited to, saline, phosphate buffer solution, Hank's balanced salts, Tris buffered saline, Hepes buffered saline and combinations thereof. In addition, the tissue can be minced in any standard cell culture medium known to those having ordinary skill in the art, either in the presence or absence of serum. Prior to depositing the suspension of minced tissue on the scaffold or at the site of tissue injury, the minced tissue suspension can be filtered and concentrated, such that only a small quantity of physiological buffering solution remains in the suspension to prevent the tissue particles from drying out, and the minced tissue particles can be directly applied to the scaffold or site of injury. Preferably, the minced tissue particles are loaded at a concentration in the range of approximately 1 to 100 mg/cm², and more preferably in the range of about 1 to 20 mg/cm².

The suspension of minced living tissue can be used to create a tissue repair implant according to the present invention by depositing the suspension of living tissue upon a biocompatible scaffold, such that the tissue and the scaffold become associated. Preferably, the tissue is associated with at least a portion of the scaffold. The tissue repair implant can be implanted in a subject immediately, or alternatively, the construct can be incubated under sterile conditions for a duration and under conditions that are effective to maintain the viability of the tissue sample. In embodiments where the construct is incubated, the incubation conditions can vary, but preferably, the construct is incubated for a duration in the range of 1 hour to 6 weeks, and more preferably between about 1 week and 6 weeks, at a temperature in the range of about 20 to 40° C., and in an atmosphere containing between about 5 and 10% carbon dioxide ($CO_2$) and high humidity, e.g., approximately 100% humidity.

A kit can be used to assist in the preparation of the tissue repair implants of the present invention. According to the present invention, the kit includes a sterile container that houses one or more biocompatible scaffolds, a harvesting tool for collecting the living tissue sample from a subject, and one or more reagents for sustaining the viability of the tissue sample. Suitable reagents for sustaining the viability of the tissue sample include a physiological solution, such as for example, saline, phosphate buffering solution, Hank's balanced salts, standard cell culture medium, Dulbecco's modified Eagle's medium, ascorbic acid, HEPES, nonessential amino acid, L-proline, fetal bovine serum, autologous serum, and combinations thereof. The kit can also include a processing tool for dividing the tissue into minced tissue particles, or alternatively, the harvesting tool can be adapted to collect the tissue sample and to process the sample into finely divided tissue particles. The kit can, optionally, also include a delivery device for transferring the scaffold from the sterile container to a subject for implantation.

A biological component may, optionally, be incorporated within the tissue repair implants of the present invention. Preferably, the biological component is incorporated within, or coated on, the scaffolds disclosed above. In embodiments where the biological component is coated onto the scaffold, the biological component is preferably associated with at least a portion of the scaffold. By way of nonlimiting example, the biocompatible scaffold can include an adhesion agent for anchoring the suspension of minced tissue fragments to the scaffold. Preferably, the adhesion agent is an anchoring agent, a cross-linking agent (i.e., chemical or physical), and combinations thereof.

Suitable anchoring agents include, but are not limited to, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, Matnigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

Suitable cross-linking agents include, for example, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light (e.g., blue light and UV light), pH, temperature, and combinations thereof.

The biological components used in the present invention can also be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and Surgicel®, available from Ethicon, Inc.), hyaluronic acid, and compounds or agents that suppress the immune system (e.g., immunosuppressants).

By way of example, other types of effectors present within the implant of the present invention can include heterologous or autologous growth factors, proteins (including matrix proteins), peptides, antibodies, enzymes, platelets, glycoproteins, hormones, cytokines, glycosaminoglycans, nucleic acids, analgesics, viruses, virus particles, and cell types. It is understood that one or more effectors of the same or different functionality may be incorporated within the implant.

Examples of suitable effectors include the multitude of heterologous or autologous growth factors known to promote healing and/or regeneration of injured or damaged tissue. These growth factors can be incorporated directly into the biocompatible scaffold, or alternatively, the biocompatible scaffold can include a source of growth factors, such as for example, platelets. Exemplary growth factors include, but are not limited to, TGF-β, bone morphogenic protein, cartilage-derived morphogenic protein, fibroblast growth factor, platelet-derived growth factor, vascular endothelial cell-derived growth factor (VEGF), epidermal growth factor, insulin-like growth factor, hepatocyte growth factor, and fragments thereof. Suitable effectors likewise include the agonists and antagonists of the agents noted above. The growth factor can also include combinations of the growth factors listed above. In addition, the growth factor can be autologous growth factor that is supplied by platelets in the blood. In this case, the growth factor from platelets will be an undefined cocktail of various growth factors.

The proteins that may be present within the implant include proteins that are secreted from a cell or other biological source, such as for example, a platelet, which is housed within the implant, as well as those that are present within the implant in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one of ordinary skill in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The biocompatible scaffolds of the present invention can also have cells incorporated therein. Suitable cell types that can serve as effectors according to this invention include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, and bone marrow cells. Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The tissue implants of the invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the biocompatible scaffold of the tissue repair implant, the implant can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One of ordinary skill in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One of ordinary skill in the art will appreciate that the identity of the biological component may be determined by a surgeon, based on principles of medical science and the applicable treatment objectives.

The biological component or effector of the issue repair implant can be incorporated within the scaffold before or after manufacture of the scaffold, or before or after the surgical placement of the implant.

Prior to surgical placement, the biocompatible scaffold can be placed in a suitable container comprising the biological component. After an appropriate time and under suitable conditions, the scaffold will become impregnated with the biological component. Alternatively, the biological component can be incorporated within the scaffold by, for example, using an appropriately gauged syringe to inject the biological agent(s) into the scaffold. Other methods well known to those of ordinary skill in the art can be applied in order to load a scaffold with an appropriate biological component, such as mixing, pressing, spreading, centrifuging and placing the biological component into the scaffold. Alternatively, the biological component can be mixed with a gel-like carrier prior to injection into the scaffold. The gel-like carrier can be a biological or synthetic hydrogel, including an alginate, a cross-linked alginate, hyaluronic acid, collagen gel, poly(N-isopropylacrylamide), poly(oxyalkylene), a copolymer of poly(ethylene oxide)-poly(propylene oxide), poly(vinyl alcohol) and blends thereof.

Following surgical placement, an implant wherein the biocompatible scaffold is devoid of any biological component can be infused with biological agent(s), or an implant wherein the scaffold includes at least one biological component can be augmented with a supplemental quantity of the biological component. One method of incorporating a biological component within a surgically installed implant is by injection using an appropriately gauged syringe.

The amount of the biological component included with a biocompatible scaffold will vary depending on a variety of factors, including the size of the scaffold, the material from which the scaffold is made, the porosity of the scaffold, the identity of the biologically component, and the intended purpose of the tissue repair implant. One of ordinary skill in the art can readily determine the appropriate quantity of biological component to include within a biocompatible scaffold for a given application in order to facilitate and/or expedite the healing of tissue. The amount of biological component will, of course, vary depending upon the identity of the biological component and the given application.

In another embodiment, the tissue repair implant can include an additional retaining element that is placed over the tissue-laden scaffold. Preferably, in this embodiment, at least a portion of the tissue suspension is associated with at least a portion of the outer surface of the scaffold, such that the tissue suspension is "sandwiched" between the biocompatible scaffold and the retaining element. The retaining element can be formed from virtually any biocompatible material, and in one embodiment, the retaining element can be formed using tissue grafts, including grafts obtained from allogeneic tissue, autogeneic tissue, and xenogeneic tissue, an additional biocompatible scaffold selected from the biocompatible scaffolds disclosed above, and combinations thereof. In another embodiment, the retaining element can be a porous mesh, a porous mesh-like material, such as for example, a knit, a weave, a nonwoven, or a thin, perforated elastomeric sheet having pores or perforations to allow tissue ingrowth. The thin, perforated elastomeric sheets are preferably constructed from collagen or silk or blends or copolymers of polylactic acid (PLA), polyglycolic acid (PGA), polycaprolactone (PCL) and polydioxanone (PDO). The type of retaining element used can vary according to the desired tissue repair. By way of non-limiting example, in one embodiment for meniscus repair, the retaining element can be a mesh-reinforced foam. In embodiments for ACL and cartilage repair, the retaining element can be a mesh structure. In embodiments where the retaining element is an allograft or an autograft, preferably the allograft or autograft is selected from periosteum, perichondrium, iliotibial band or fascia lata, gracilis tendon, semitendinosis tendon, patellar tendon, synovium and combinations thereof. In embodiments where the retaining element is a xenograft, the xenograft is preferably selected from the corresponding anatomical structure for small intestine, periosteum, perichondrium, iliotibial band or fascia lata, gracilis tendon, semitendonous tendon, patellar tendon, synovium, and combinations thereof. These retaining elements can be placed over the biocompatible scaffold, or alternatively, the retaining element can be affixed, such as for example, by suturing or stapling, the implant to act as a retaining element. One of ordinary skill in the art will appreciate that additional processing of the retaining element, such as for example, the placement of holes within the retaining element, may be determined by a surgeon, based on principles of medical science and the applicable treatment objectives.

In yet another embodiment, an electrostatically spun fabric barrier may be added to the implant to act as a barrier to hyperplasia and tissue adhesion, thus reducing the possibility of postsurgical adhesions. The fabric barrier is preferably in the form of dense fibrous fabric that is added to the implant. Preferably, the fibrous fabric is comprised of small diameter fibers that are fused to the top and/or bottom surface of the biocompatible scaffold. This enables certain surface properties of the structure, such as porosity, permeability, degradation rate and mechanical properties, to be controlled.

One of ordinary skill in the art will appreciate that the fibrous fabric can be produced via an electrostatic spinning process in which a fibrous layer can be built up on lyophilized foam and nonwoven surfaces. This electrostatic spinning process may be conducted using a variety of fiber materials. Exemplary fiber materials include aliphatic polyesters. A variety of solvents may be used as well, including those identified above that are useful to prepare the polymer solution that forms the foam component.

The composition, thickness, and porosity of the fibrous layer may be controlled to provide the desired mechanical and biological characteristics. For example, the bioabsorption rate of the fibrous layer may be selected to provide a longer or shorter bioabsorption profile as compared to the underlying biocompatible scaffold. Additionally, the fibrous layer may provide greater structural integrity to the composite so that mechanical force may be applied to the fibrous side of the structure. In one embodiment the fibrous layer could allow the use of sutures, staples or various fixation devices to hold the composite in place. Generally, the fibrous layer has a thickness in the range of about 1 micron to 1000 microns. However, for some applications such as rotator cuff and meniscus injury repair, the fibrous layer has a thickness greater than about 1.5 mm.

The tissue repair implants of the present invention can be used in a variety of surgical and non-surgical applications. In some surgical applications, such as for use in the repair of a variety of tissues including a torn ligament, tendon, rotator cuff, nerve, skin, cartilage, or meniscus, the tissue implants of the invention must be able to be handled in the operating room, and they must be able to be sutured or otherwise fastened without tearing. Additionally, the implants should have a burst strength adequate to reinforce the tissue, and the structure of the implant can be suitable to encourage tissue ingrowth. By way of non-limiting example, the scaffolds of the present invention can be highly porous to allow cell growth therein. Preferably, the median pore size is in the range of about 100 to 500 microns. In these embodiments, the scaffold should be sufficiently pliable to accommodate tissue growth within the interior region of the scaffold, so that the geometry of the scaffold can be remodeled as tissue ingrowth increases. Accordingly, in the present invention, tissue can be grown on the surface of the biocompatible scaffold, or alternatively, tissue can be grown into and on the surface of the biocompatible scaffold, such that the tissue becomes embedded in and integrated with the scaffold.

In one embodiment of the present invention, the tissue repair implant is used in the treatment of a tissue injury, such as injury to a ligament, tendon, nerve, skin, cartilage or meniscus. Repairing tissue injuries involves the steps of obtaining a sample of living tissue by any of the variety of techniques known to those having ordinary skill in the art, processing that sample of living tissue under sterile conditions, such as for example by cutting the tissue, to create at least one minced, finely divided tissue particle, depositing the tissue sample upon the biocompatible scaffold, such that the tissue sample becomes associated with the scaffold to form a tissue repair implant, and placing the tissue repair implant in a desired position relative to the tissue injury. Repairing tissue injuries may also involve placing the scaffold at the site of tissue injury and then depositing the fine tissue particles onto the scaffold. The cells in the tissue particles associated with the scaffold can migrate to the scaffold and begin proliferating and integrating with surrounding tissue at the site of implantation, thereby repairing the tissue injury. This method for repairing tissue injuries can include an additional, optional step. Prior to the step of placing the tissue repair implant in a desired position relative to the tissue injury, the scaffold and associated tissue particles can be incubated for a duration and under conditions effective to allow cells within the tissue particles to migrate from the tissue and begin populating the scaffold.

The tissue samples used in the present invention are obtained from a donor (autogenic, allogeneic, or xenogeneic) using appropriate harvesting tools. The tissue samples can be finely minced and divided into small particles either as the tissue is collected, or alternatively, the tissue sample can be minced after it is harvested and collected outside the body. In embodiments, where the tissue sample is minced after it is harvested, the tissue samples can be weighed and then washed three times in phosphate buffered saline. Approximately 300 to 500 mg of tissue can then be minced in the presence of a small quantity, such as, for example, about 1 ml, of a physiological buffering solution, such as, for example, phosphate buffered saline, or a matrix digesting enzyme, such as, for example, 0.2% collagenase in Hams F12. Mincing the tissue divides the tissue into particles or small pieces of approximately 1 $mm^3$. Mincing the tissue can be accomplished by a variety of methods. In one embodiment, the mincing is accomplished with two sterile scalpels using a parallel direction, and in another embodiment, the tissue can be minced by a processing tool that automatically divides the tissue into particles of a desired size. In one embodiment, the minced tissue can be separated from the physiological fluid and concentrated using any of a variety of methods known to those having ordinary skill in the art, such as for example, sieving, sedimenting or centrifuging. In embodiments where the minced tissue is filtered and concentrated, the suspension of minced tissue preferably retains a small quantity of fluid in the suspension to prevent the tissue from drying out. In another embodiment, the suspension of minced tissue is not concentrated, and the minced tissue can be directly delivered to the site of tissue repair via a high concentration tissue suspension or other carrier such as for example, a hydrogel, fibrin glue, or collagen. In this embodiment, the minced tissue suspension can be covered by any of the biocompatible scaffolds described above to retain the tissue fragments in place.

The minced tissue can then be distributed onto a scaffold using a cell spreader so as to cover the entire scaffold. In a preferable embodiment for meniscus and cartilage repair, the minced tissue is spread onto 4×5 cm scaffolds that have been presoaked in Dulbecco's modified Eagles medium (DMEM) so as to cover the entire scaffold. Optionally, the tissue particles can be adhered to the scaffolds using any of the adhesive agents described above, such as, for example, fibrin glue or platelet rich plasma. In embodiments using fibrin glue or platelet rich plasma, a few microliters of thrombin can be placed on the scaffolds, prior to distribution of fibrinogen or platelet rich plasma on the scaffolds, and allowed to set. Once the tissue particles and any additional agents have been deposited on the scaffold, the tissue repair implant can then implanted immediately, or alternatively, the implant can be cultured in vitro for a duration and under conditions sufficient to allow the cells in the tissue particles to migrate from the tissue particles onto the scaffold. In an embodiment where the tissue repair implant is incubated prior to implantation, the implant is preferably cultured in vitro for approximately 1-3 weeks in a chondrocyte growth medium, such as for example, DMEM-high glucose, supplemented with 20% fetal calf serum (FCS), 10 mM HEPES, 0.1 mM nonessential amino acids, 20 mg/ml of L-proline, 50 mg/ml ascorbic acid, 100 mg/ml penicillin, 100 mg/ml of streptomycin and 0.25 mg/ml of amphotericin B.

The methods of repairing tissue injuries using the tissue implants according to the present invention can be conducted during a surgical operation to repair the tissue injury. Alternatively, the steps of processing the tissue sample to create minced, finely divided tissue particles, depositing the tissue particles upon the scaffold to form a tissue repair implant, and/or incubating the tissue repair implant prior to implantation can be conducted at another, sterile location prior to surgical placement of the implant relative to the site of injury.

The implants used to repair injured tissue can be of a size and shape such that they match the geometry and dimensions of a desired portion or lesion of the tissue to be treated. The implant can be sized and shaped to produce the necessary geometry by numerous techniques including cutting, folding, rolling, or otherwise manipulating the implant. As noted above, the biological component may be added to the scaffold during or after manufacture of the scaffold or before or after the implant is installed in a patient. An additional quantity of the biological component may be added after the implant is installed. Once access is made into the affected anatomical site (whether by minimally invasive, open or mini-open surgical technique), the implant can be affixed to a desired position relative to the tissue injury, such as within a tear or lesion. Once the implant is placed in the desired position or lesion, it can be affixed by using a suitable technique. In one aspect, the implant can be affixed by a chemical and/or mechanical fastening technique. Suitable chemical fasteners include glues and/or adhesive such as fibrin glue, fibrin clot, and other known biologically compatible adhesives. Suitable mechanical fasteners include sutures, staples, tissue tacks, suture anchors, darts, screws, pins and arrows. It is understood that combinations of one or more chemical and/or mechanical fasteners can be used. Alternatively, one need not use any chemical and/or mechanical fasteners. Instead, placement of the implant can be accomplished through an interference fit of the implant with an appropriate site in the tissue to be treated.

In another embodiment, the tissue repair implant is useful in surgical techniques that repair ligaments, tendons, skin and/or nerves.

In one use, the tissue repair implant can be for repair and to augment tissue loss during tendon or ligament repair surgery or it can be used as a stand alone device. In the case of repair, tendon or ligament ends are approximated through appropriate surgical techniques and the tissue repair implant is used around the joined end to give more mechanical support and to enhance the healing response. As a result of the healing process, the tendon or ligament tissue grows within the implant device, eventually maturing into a tissue with similar mechanical properties to that of native tissue. The implant provides the mechanical support that is initially necessary to ensure proper healing, and it also serves as a guide for tissue regeneration. In another use as a stand alone device, the ruptured tissue is removed, and the tissue repair implant with minced tissue serves to replace the function of the damaged tissue. The ruptured tissue can be the tissue source used for healing damaged tissue.

In embodiments where the tissue repair implant is used to repair ligament tissue, the tissue repair implant can be used for tissue augmentation, or alternatively, as a stand-alone device. In embodiments where the tissue repair implant is used for augmentation, the tissue repair implant can be used in conjunction with any of a variety of standard, established repair techniques known to those having ordinary skill in the art. In embodiments where the tissue repair implant is used for augmentation during ACL repair, surgeons currently use an autograft consisting of ligament tissue, bone-patellar tendons, tendon-bone tendons, hamstring tendons, or iliotibial band to repair tissue, and the tissue repair implant of the present invention can be placed either around the autograft, surrounded by the autograft, or alongside the autograft. In embodiments where the tissue repair element is used as a stand-alone device, the ruptured ligament can be removed and completely replaced by the tissue repair implant. In this case, the tissue repair implant can be affixed to bone at each end of the implant. In the case of ACL repair, one end of the implant can be stabilized at the original origin site of the femur, while the other end can be placed at the original insertion site on the tibia.

The tissue repair implant can be utilized in a variety of configurations. For example, the implant can be folded or stacked in multiple laminates or it can be rolled into the shape or a tube-like structure. Tendon or ligament ends can be joined, for example, by suturing, stapling, clipping, adhering, or anchoring, the implant to ends of the implant. In some embodiments where the tissue repair implant is used to repair tendons, such as for example, rotator cuff repair, the surgeon can use the tissue repair implant to assist in the reapproximation of the torn rotator cuff to a bony trough through the cortical surface of the greater tuberosity. Often times, in older patients, the rotator cuff tissue is thin and degenerate and/or the quality of the humerus is osteoporotic. Therefore, in order to increase the strength of the attachment to the bony trough, the tissue repair implant can be placed on top of the tendon, such that the sutures would pass through both the scaffold and tendon, or alternatively, the tissue repair implant can be used on top of the bone bridge to prevent the sutures from pulling out of the bone. In either embodiment, the tissue repair implant provides suture retention strength. In situations where the quality of the rotator cuff is so degenerate that the tissue cannot be reapproximated to the humerus, the tissue repair implant can serve as a bridge, wherein one end of the implant can be joined to the remaining tendon while the other end can be attached to the bone.

In another variation, the implant can be used to repair or replace the sheath of a tendon. To do so, the implant is sutured or otherwise joined to the connective tissue, such as the periosteum, synovium, or muscle, and wrapped around the tendon. This construction allows free gliding of the tendon within the sheath formed by the implant. The implant provides the necessary structural support following surgery. Over time, however, the implant in this embodiment can be resorbed and replaced by new tissue.

The implants of the invention can also be used for organ repair replacement or regeneration strategies that may benefit from these unique tissue implants. For example, these implants can be used for spinal disc, cranial tissue, dura, nerve tissue, liver, pancreas, kidney, bladder, uterus, esophagus, liver spleen, cardiac muscle, skeletal muscle, skin, fascia, pelvic floor, stomach, tendons, cartilage, ligaments, and breast tissues.

In yet another embodiment, the implants of the present invention can be used to create a biological assay for measuring the effect of a substance on living tissue. In this embodiment, tissue constructs are created, as described above, by providing a sterile, biocompatible scaffold, obtaining a sample of living tissue, processing the sample of living tissue under sterile conditions to form a suspension of minced tissue having minced tissue fragments and a physiological buffering solution, and depositing the suspension of minced tissue on the biocompatible scaffold such that the suspension of minced tissue and the scaffold become associated. The tissue construct is incubated under conditions that are effective to allow cells within the minced tissue to populate the scaffold. The tissue construct can then be contacted with the substance that is to be tested, and the effect(s) of that substance can be determined. These tissue constructs can be used to determine and/or test the biological responses to a test substance, such as for example, cell viability, growth, migration, differentiation and maintenance of cell phenotype, metabolic activity, induction or repression. These biological responses can be assayed using any of a variety of techniques known to those having ordinary skill in the art, such as for example, proliferation assay, cell migration assay, protein assay, gene expression assay, viability assay, calorimetric assay or metabolic assay. By way of non-limiting example, the expression of a selected gene(s) or gene products typically expressed by the tissue of the tissue construct, such as for example, the expression of type II, type IX or type XI collagen expressed by chondrocytes, using a variety known assays, such as for example, northern blot analysis, RNAse protection assays, polymerase chain reaction (PCR), western blot analysis and enzyme-linked immunoabsorbant assay (ELISA). Suitable substances that can be tested using the tissue constructs of the present invention include, but are not limited to, drugs, pharmaceutical compositions, chemicals, microbes, elements, cytokines, growth factors, hormones, antibodies, peptides, ligands, antagonists of membrane-bound receptors, and combinations thereof.

The implants of the present invention can also be used as a delivery device for a therapeutic, wherein the therapeutic is the minced tissue, which includes a combination of cells, extracellular matrix and inherent growth factors. The scaffold portion of the implant can allow for hormones and proteins to be released into the surrounding environment.

The methods of repairing tissue injuries using the tissue implants according to the present invention can be conducted during a surgical operation to repair the tissue injury. A patient is prepared for tissue repair surgery in a conventional manner using conventional surgical techniques. Tissue repair is performed at the site of injured tissue using the tissue repair implants of the present invention. The tissue sample used to form the tissue repair implant is obtained from the patient (or another donor) using appropriate tools and techniques. The tissue sample is finely minced and divided into at least one tissue particle having a particle size in the range of about 0.1 to 3 $mm^3$. The tissue can be minced using a conventional mincing technique such as two sterile scalpels used in a parallel direction. Between about 300 to 500 mg of tissue is minced in the presence of about 1 ml of a physiological buffering solution, depending on the extent of the tissue injury at the site of repair. The minced tissue is filtered and concentrated to separate the minced tissue particle from the physiological buffering solution. The minced tissue can be concentrated using any of a variety of conventional techniques, such as for example, sieving, sedimenting or centrifuging. The minced tissue particles are then distributed using a cell spreader onto a 4×5 cm biocompatible scaffold that has been soaked in Dulbecco's modified Eagles medium (DMEM). An adhesion agent can be added to the biocompatible scaffold and the minced tissue particles. The tissue repair implant is implanted at the site of tissue injury, either immediately or after a period of in vitro incubation. Final wound closure is performed in a conventional manner using conventional surgical techniques.

The following examples are illustrative of the principles and practice of this invention. Numerous additional embodiments within the scope and spirit of the invention will become apparent to those skilled in the art.

Example 1

Healthy cartilage tissue from articulating joints was obtained from bovine shoulders. The cartilage tissue, which was substantially free of bone tissue, was minced using scalpel blades to obtain small tissue fragments in the presence of 0.2% collagenase. The size of the tissue fragments varied but on average should be approximately 1×1 mm in dimension.

Figure 1B:
FIG. 1B is a photomicrograph that demonstrates that the migrating cells of FIG. 1A retain their phenotype and the migrating cells produce cellular matrix that stains positive for sulfated glycosaminoglycan using the Safranin O stain.

The minced tissue was then distributed uniformly on a 4×5 cm synthetic bioresorbable polycaprolactone/polyglycolic acid (PCL/PGA) scaffold. Ethylene oxide sterilized polymer scaffolds, were pre-soaked for 4 hours in Dulbecco's Modified Eagle's Medium prior to distribution of tissue fragments. The scaffold loaded with minced fragments was then placed in a 10 cm cell culture dish containing chondrocyte growth medium. The chondrocyte growth medium consisted of Dulbecco's modified eagles medium (DMEM-high glucose) supplemented with 20% fetal calf serum (FCS), 10 mM HEPES, 0.1 mM nonessential amino acids, 20 mg/ml of L-proline, 50 mg/ml ascorbic acid, 100 mg/ml penicillin, 100 mg/ml of streptomycin and 0.25 mg/ml of amphotericin B. The growth medium was replenished every other day. Scaffolds were cultured at 37° C. in a cell culture incubator. Six weeks following culture samples were removed and analyzed for cell distribution and migration within the scaffolds and for production of cartilage like matrix. FIG. 1 demonstrates that cells migrate extensively into the polymer scaffolds from the minced cartilage tissue fragments (FIG. 1A). The migrating cells retain their phenotype and produce matrix that stained positive for the sulfated glycosaminoglycans using the Safranin O stain (FIG. 1B).

Example 2

Figure 2A:
FIG. 2A is a photomicrograph that demonstrates that cells within the minced tissue loaded on the biocompatible scaffolds, following implantation into SCID mice, have proliferated and filled the entire scaffold.
Figure 2B:
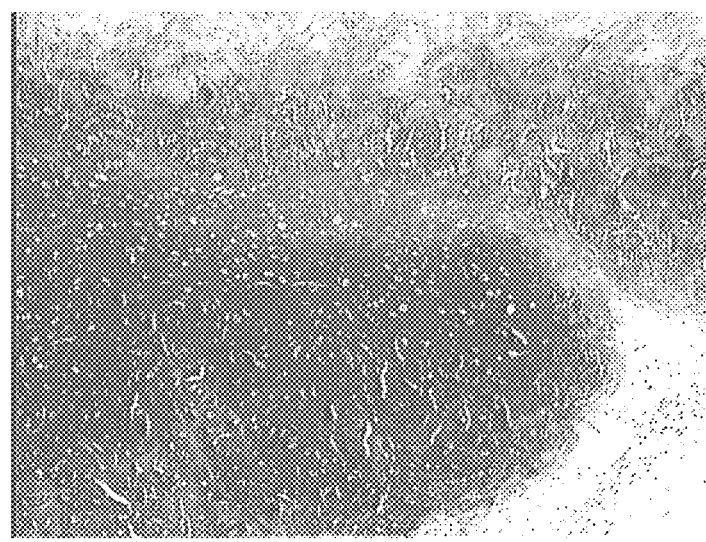
FIG. 2B is a photomicrograph that demonstrates that cells within the minced tissue, following implantation into SCID mice, are chondrocyte-like and are surrounded by an abundant matrix that stains positive for Safranin O.

The bioresorbable scaffolds containing minced cartilage tissue and cells from Example 1 were also implanted into SCID mice. The objective was to evaluate the chondrocytic ingrowth of minced cartilaginous tissues into polymer scaffolds in vivo. Polymer scaffolds 5 mm in diameter, were subcutaneously implanted bilaterally in the lateral thoracic region of SCID mice. The implanted scaffold was permitted to support cell growth for four weeks. The subcutaneous implantation sites with their overlying skin were then excised and preserved in 10% buffered formalin fixative. Following fixation, each implantation site was processed for histology. Histological sections were stained with Hematoxylin and eosin, and Safranin-O. FIGS. 2 A and B show that abundant cells were distributed within the scaffold. The cells displayed chondrocyte-like morphology, as evidenced by the intense positive staining for Safranin O of the synthesized matrix.

Example 3

Figure 3A:
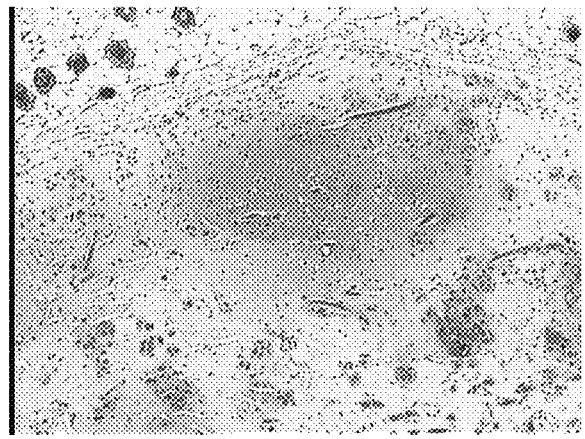
FIG. 3A is a photomicrograph that illustrates a scaffold loaded with minced tissue.
Figure 3B:
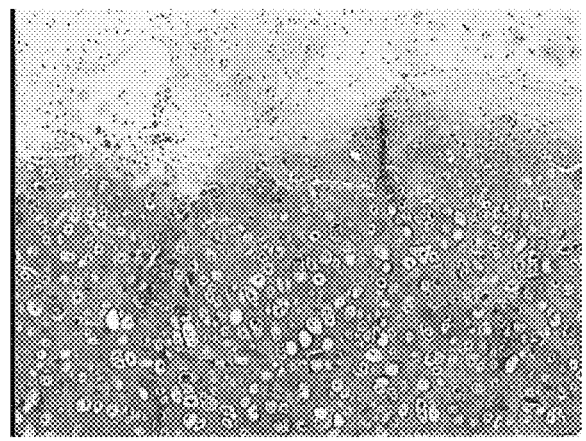
FIG. 3B is a photomicrograph that illustrates a scaffold loaded with minced tissue and platelet rich plasma (PRP) and demonstrates that growth factors in the PRP are beneficial in promoting the migration of chondrocyte cells from the minced tissue and in promoting maintenance of differentiated phenotype of the chondrocyte cells within the scaffolds.

Minced cartilage tissue prepared according to the method described in Example 1 was distributed uniformly on a 4×5 cm synthetic bioresorbable polycaprolactone/polyglycolic acid (PCL/PGA) scaffold. Minced cartilage tissue fragments were adhered to the scaffolds with 1 mL of platelet rich plasma (PRP, Human). Sixty microliters (60 units) of thrombin were used to induce clot formation in the PRP. Control scaffolds loaded with minced cartilage fragments alone and scaffolds loaded with minced cartilage fragments adhered by PRP, were cultured in vitro for 1 week, and then implanted into SCID mice as described in the Example 2. FIG. 3A is a photomicrograph of a control scaffold loaded with minced tissue. FIG. 3B is a photomicrograph depicting a scaffold loaded with minced tissue and PRP. FIG. 3B demonstrates that PRP is beneficial in promoting the migration of the chondrocyte cells, and PRP is also beneficial in promoting the maintenance of the differentiated phenotype of the chondrocyte cells within the scaffolds. The migrating cells retain their phenotype and produce matrix that stained positive for the sulfated glycosaminoglycans using the Safranin O stain (FIG. 3B).

Example 4

Figure 4:
FIG. 4 is a photomicrograph that demonstrates that autologous cell dispersion (derived from skin) is present histologically as keratinocyte islands.
Figure 4:
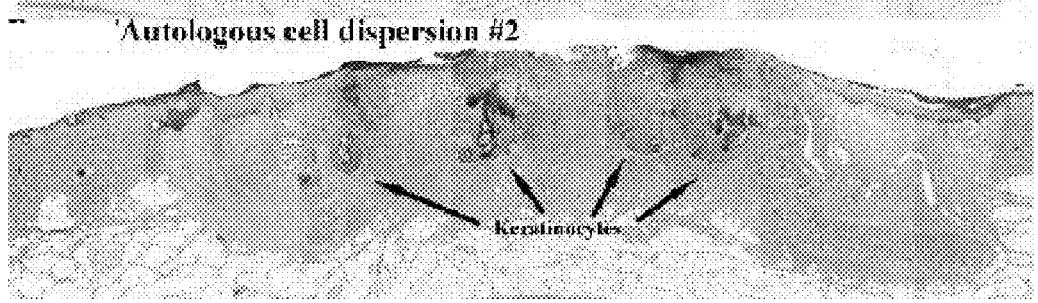

Healthy full-thickness skin samples, collected from 1×1 cm wounds created on the dorsal side of the pigs, were immediately placed in 50 ml conical tubes containing DMEM with 10× antibiotics/antimycotics. Tissue samples were rinsed once in PBS containing 10× antibiotic/antimycotics followed by an additional rinsing step with PBS containing 1× antibiotics/antimycotics. The tissue was minced aseptically using a scalpel blade in a laminar flow hood. Dispersed skin samples were subjected to enzymatic digestion with 1 ml of 0.25% collagenase/0.25% dispase at 37° C. for 15 min (Autologous cell dispersion #1). Another set of samples were first digested with 500 µl of 0.25% trypsin for 10 min, then washed with PBS to remove trypsin, and then incubated with 1 ml of 0.25% collagenase/0.25% dispase at 37° C. for 15 min (Autologous cell dispersion #2). Following digestion, the samples were centrifuged at 2500 rpm for 5 min. The supernatant was aspirated and discarded. Dispersed, partially digested skin samples were washed once in PBS and then re-suspended in 500 µl of PBS. Approximately 20 µl of cell suspension was distributed evenly in the wound bed and bioresorbable scaffold was carefully applied on the top of dispersed cells making sure not to dislodge the cell suspension. Dispersed cells could be distributed evenly on the scaffold and placed onto the wound bed. FIG. 4 demonstrates that autologous cell dispersion was present histologically as keratinocyte "islands," some of which had migrated throughout the scaffold towards the wound surface.

Example 5

Figure 5A:
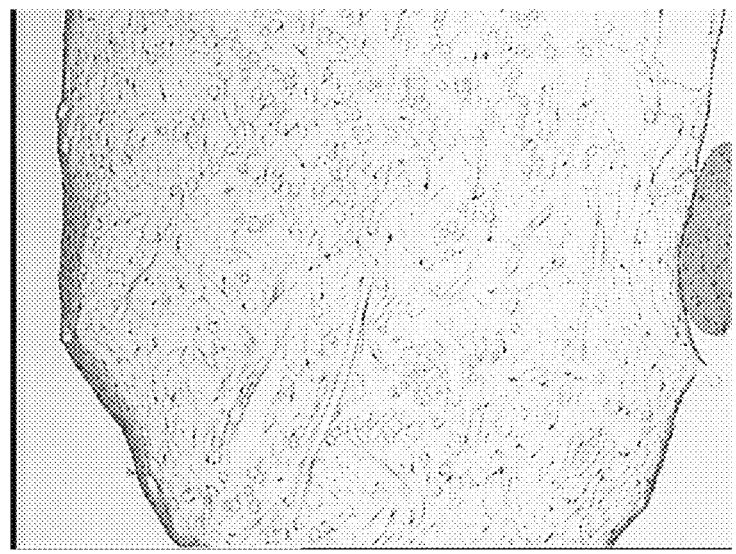
FIG. 5A is a photomicrograph that demonstrates the extensive migration of cells into the polymer scaffolds after incubating for 6 weeks in culture the biocompatible scaffolds having minced anterior cruciate tissue fragments that have been treated with collagenase.
Figure 5B:
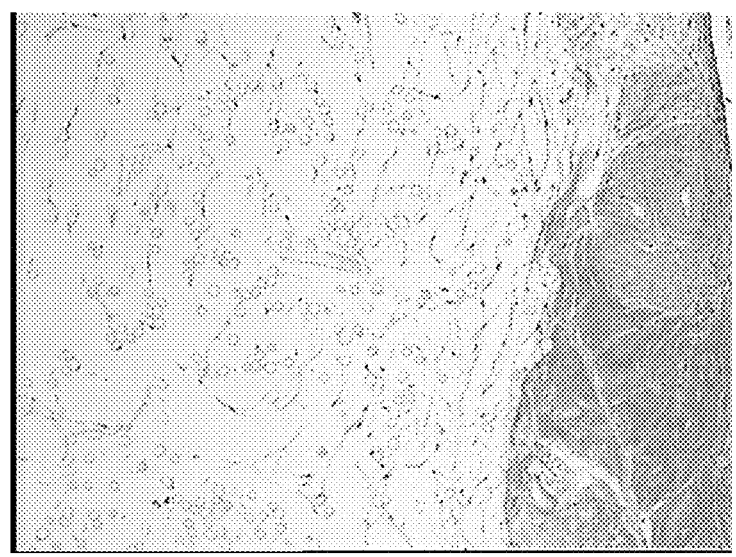
FIG. 5B is a photomicrograph that demonstrates the extensive migration of cells into the polymer scaffolds after incubating for 6 weeks in culture the biocompatible scaffolds having minced anterior cruciate tissue fragments treated without collagenase.

Healthy anterior cruciate ligament tissue was obtained from bovine knees. The ligament tissue was minced using scalpel blades and/or scissors to obtain small tissue fragments. While the size of the tissue fragments varied, the average particle size was approximately 1 mm$^3$ in dimension. In this example, the ligament was minced with and without 0.2% collagenase. The minced tissue was then distributed uniformly on a 4×5 cm synthetic bioresorbable polycaprolactone/polyglycolic acid PGA/PCL scaffold or polylactic acid/polyglycolic acid (PLA/PGA) scaffold. The scaffolds were sterilized in 70% ethanol for our hour and washed three times with sterile PBS. The scaffolds were then pre-soaked for 1-2 hours in Dulbecco's Modified Eagle's Medium with 1× antibiotic-antimycotic prior to distribution of tissue fragments. The scaffold loaded with minced fragments was then placed in a 10 cm cell culture dish containing growth medium, which consisted of Dulbecco's modified eagles medium (DMEM-high glucose) supplemented with 20% fetal calf serum (FCS), 100 mg/ml penicillin, 100 mg/ml of streptomycin and 0.25 mg/ml of amphotericin B. Scaffolds with the minced tissue were cultured at 37° C. in a cell culture incubator and the growth medium was exchanged every other day. Three and six weeks following culture, samples were removed and analyzed for cell distribution and migration within the scaffolds. FIG. 5 demonstrates cells migrating extensively into the polymer scaffolds after 6 weeks in culture from the minced anterior cruciate tissue fragments treated with collagenase (FIG. 5A) and without collagenase (FIG. 5B).

Example 6

Figure 6A:
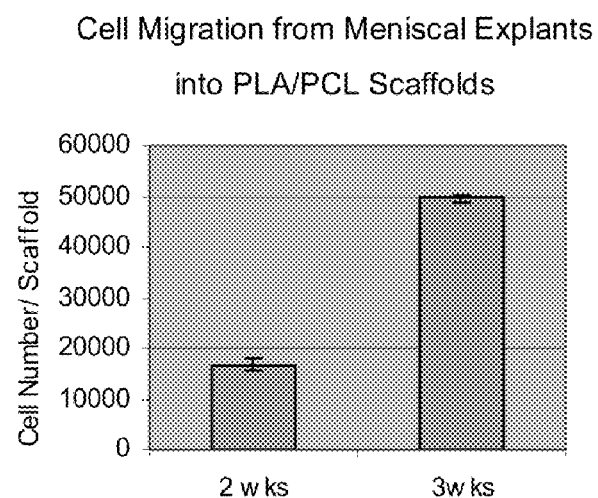
FIG. 6A is a graph that demonstrates that cells in a meniscal explant sample migrate extensively into a polymer scaffold.
Figure 6B:
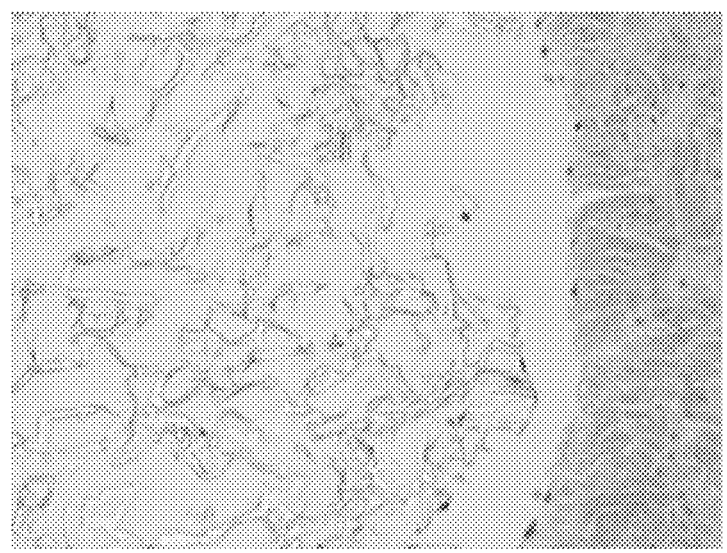
FIG. 6B is a photomicrograph that illustrates the histology of cross sections of the associated meniscal explant and biocompatible scaffolds, which demonstrates that cells in the meniscal explant sample migrate into the polymer scaffold.

Menisci were harvested from adult Goat knees and 4 mm diameter explants (2 mm thick) were taken from the white and red/white regions. A 2 mm punch biopsy was removed from the center of the explants. A bioresorbable scaffold polylactic acid/polycaprolactone (PLA/PCL) 2 mm in diameter and 2 mm thick was inserted into the center of the meniscal explant. The explants with scaffolds were cultured for 2 and 3 weeks under standard cell culture conditions with changes in media (DMEM containing 1% FBS, 1× antibiotic-antimycotic) occurring every other day. At 14 and 21 days following culture, half the samples were placed into 10% buffered formalin for histological processing. Sections were stained with Hematoxylin to visualize the cells. From the remaining samples the scaffolds were removed and cell number estimated by quantitation of DNA using the CyQuant assay. FIG. 6A demonstrates that there is cell migration into the polymer scaffolds from the meniscal explants. FIG. 6B shows the histology of cross sections of scaffolds demonstrating cell migration into scaffolds.

Example 7

Figure 7A:
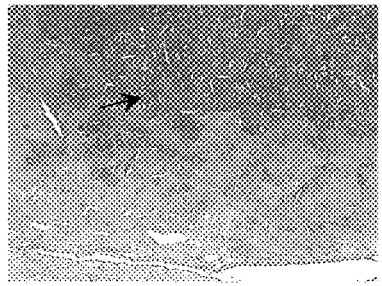
FIGS. 7A-7C are photomicrographs of histological sections of explant samples obtained following the procedure of Example 7, demonstrating the distribution and nature of tissue formed within a scaffold and grown from minced cartilage tissue fragments.
Figure 7B:
Figure 7C:
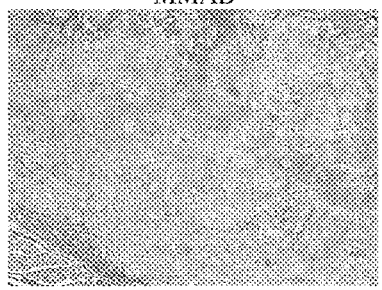
Figure 8A:
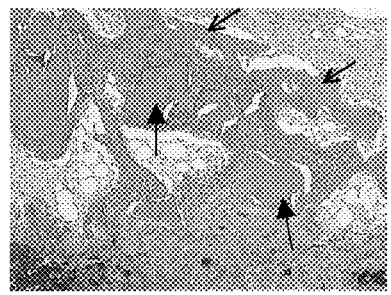
FIGS. 8A-8C are photomicrographs of histological sections of explant samples obtained following the procedure of Example 7, demonstrating the distribution and nature of tissue formed within a scaffold and grown from bone cartilage paste.
Figure 8B:
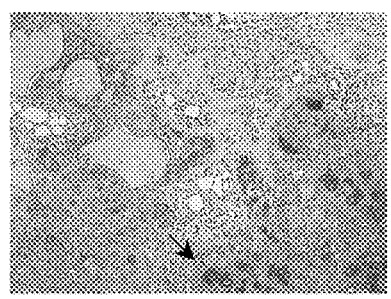
Figure 8C:
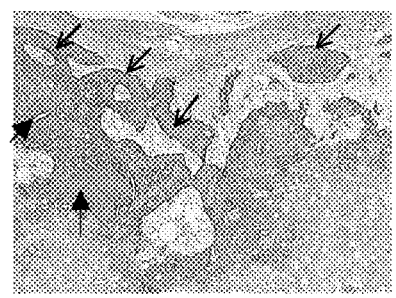

Healthy cartilage tissue and osteochondral plugs were obtained from articulating joints of bovine shoulders. Minced cartilage tissue was prepared according to the method described in Example 1. In addition, osteochondral plugs (1×1 cm) were harvested from bovine shoulders using a diamond bone saw and morselized with bone cutters to obtain bone cartilage paste. Next, 250 mg of the sample (minced cartilage or bone cartilage paste) was distributed on 2×5 cm synthetic bioresorbable (PCL/PGA) scaffolds. The scaffold loaded with minced cartilage fragments or osteochondral paste was then placed in a 10 cm cell culture dish containing chondrocyte growth medium and cultured in a cell culture incubator as described in Example 1. Three weeks following culture the samples were removed and implanted into SCID mice as described in Example 2. The objective was to evaluate the nature of tissue formed within the scaffold following implantation for 4 weeks. Histological sections were analyzed for cell distribution and for the nature of the matrix formed, within the scaffolds, by staining with Hematoxylin and eosin (H/E), Safranin O (SO) and Modified Mallory's Aniline Blue (MMAB). FIGS. 7A-7C demonstrate that cells migrate extensively into the polymer scaffolds from the minced cartilage tissue fragments and form cartilage like matrix that stains positive for Safranin O. This is particularly evident in FIG. 7B in which the darker area in the center and top of the photograph is indicative of positive staining. FIGS. 8A-8C demonstrate that cells migrate from bone cartilage paste into polymer scaffolds. However, the tissue that is formed comprises cartilage as well as new bone. The appearance of the new bone is indicated by the lighter arrows in FIG. 8C while the old bone fragments are indicated by the darker arrows in FIGS. 8 A and 8C.

Example 8

Figure 9:
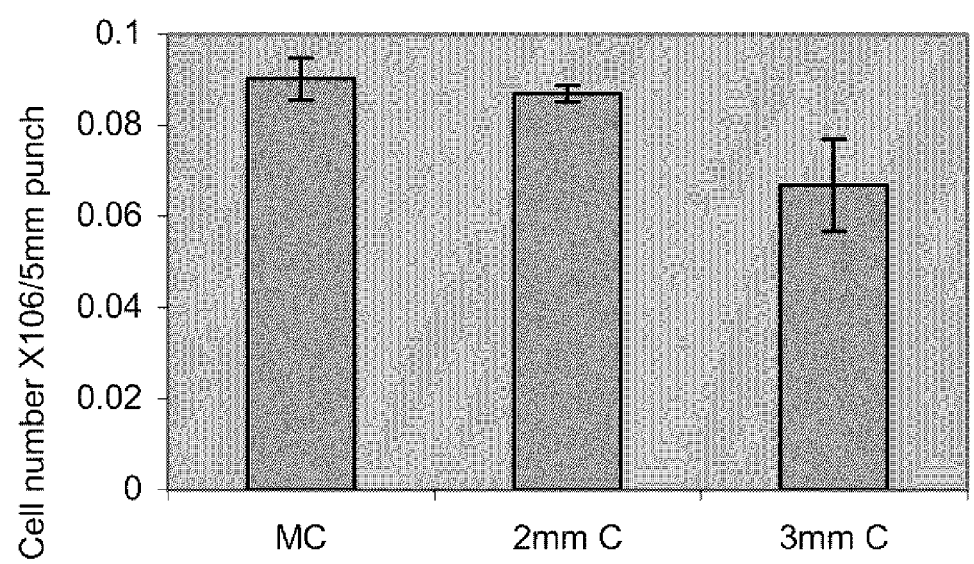
FIG. 9 is a graph comparing the numbers of cells obtained for different sizes of minced cartilage tissue fragments.
Figure 10A:
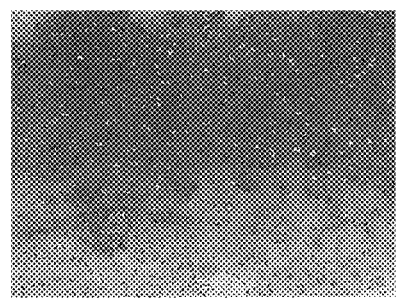
FIGS. 10A-10C are photomicrographs of histological sections of explant samples obtained following the procedure of Example 8, demonstrating the uniformity of the cartilage-like tissue obtained with minced cartilage tissue fragments of different sizes.
Figure 10B:
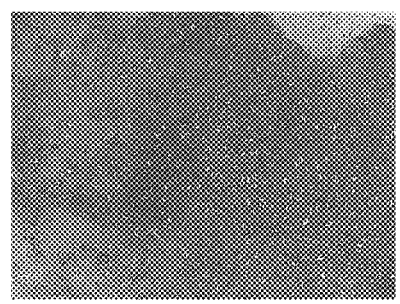
Figure 10C:
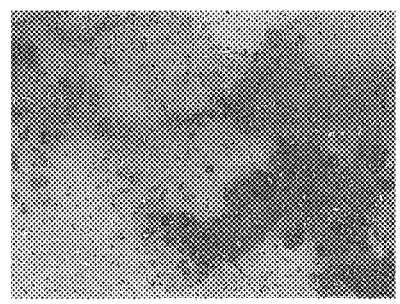

Healthy cartilage tissue was obtained from articulating joints of bovine shoulders. Minced cartilage tissue was prepared according to the method described in Example 1. Biopsy punches were used to obtain cartilage tissue fragments 2 mm and 3 mm in diameter. The thickness of these fragments was approximately 1 mm. 250 mg of minced cartilage or cartilage fragments 2 or 3 mm in diameter were distributed on 2×5 cm synthetic bioresorbable (PCL/PGA) scaffold. The scaffold loaded with cartilage fragments was then placed in a 10 cm cell culture dish containing chondrocyte growth medium and cultured in a cell culture incubator as described in Example 1. Three weeks following culture samples were removed and cell number estimated by quantitation of DNA content. 5 mm biopsy punches were also implanted into SCID mice as described in Example 2. The objective was to evaluate the optimal size of tissue fragments for this process. FIG. 9 demonstrates that the highest cell number was observed in scaffolds loaded with minced cartilage tissue and the lowest in scaffolds loaded with cartilage fragments 3 mm in diameter. FIGS. 10A-10C provide histological evaluations of scaffolds implanted into SCID mice and stained with Safranin O. These results demonstrate that uniform cartilage-like tissue (stained, darker areas) in scaffolds loaded with minced cartilage tissue and cartilage fragments 2 mm in diameter (FIGS. 10A and B). Scaffolds that were loaded with cartilage fragments 3 mm in diameter were not uniformly filled (FIG. 10C).

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tendon or ligament repair implant, comprising:
   a biocompatible porous scaffold having an aspect ratio in the range of greater than 2 and less than 100; and
   at least one minced tissue fragment derived from ligament tissue or tendon tissue, the at least one tissue fragment distributed on at least a portion of the scaffold at a concentration in the range of about 1 to about 100 mg/cm$^2$, wherein the at least one tissue fragment has a particle size in the range of about 0.1 mm$^3$ to less than 1 mm$^3$;
   wherein the scaffold is made from polymers or copolymers formed from monomers selected from the group consisting of lactide, glycolide, dioxanone, and caprolactone.

2. The implant of claim 1, wherein the scaffold has a cylindrical shape.

3. The implant of claim 1, wherein the scaffold is made from a copolymer of 95:5 lactide and glycolide.

4. The implant of claim 1, wherein the implant further includes natural polymers selected from the group consisting of collagen, fibrin, and silk.

5. The implant of claim 2, wherein the implant includes strips of collagen or silk present within an inner portion of the scaffold or on a peripheral portion of the scaffold.

6. The implant of claim 1, wherein the scaffold has a diameter in the range of about 3 to 12 mm.

7. The implant of claim 1, wherein the scaffold has a tensile strength and an elastic modulus similar to that of native tendon or ligament tissue.

8. The implant of claim 7, wherein the tensile strength of the scaffold is in the range of about 1000N to 2500N.

9. The implant of claim 7, wherein the elastic modulus of the scaffold is in the range of about 150 N/m to 200 N/m.

10. The implant of claim 1, wherein the scaffold has a slow resorption profile.

11. The implant of claim 10, wherein the resorption profile of the scaffold spans at least three months.

12. The implant of claim 1, wherein the scaffold is formed from a foam component reinforced with a mesh component.

13. The implant of claim 12, wherein the mesh component includes polydioxanone and the foam component is a copolymer of 35:65 ε-caprolactone and glycolide.

14. The implant of claim 12, wherein the scaffold has an open pore structure with pores having a size sufficient to allow cell and tissue ingrowth.

15. The implant of claim 14, wherein the pores have an average diameter in the range of about 50 to 1000 microns.

16. The implant of claim 12, wherein the foam component has a thickness in the range of about 300 microns to 2 mm.

17. The implant of claim 12, wherein the mesh component has a mesh density in the range of about 12% to 80%.

18. The implant of claim 1, wherein the scaffold is formed of a plurality of filaments.

19. The implant of claim 18, wherein the majority of fibers that form the filaments are aligned in a longitudinal direction.

20. The implant of claim 1, wherein the scaffold is formed from a material selected from the group consisting of a knit material, a woven material, and a braided material.

21. The implant of claim 12, wherein the mesh is formed on the outer surface of the scaffold.

22. The implant of claim 20, wherein the mesh is a knit or a woven structure.

23. The implant of claim 20, wherein the mesh is biodegradable and biocompatible.

24. The implant of claim 1, further comprising an autograft selected from the group consisting of ligament tissue, bone-patellar tendons, tendon-bone tendons, hamstring tendons, and iliotibial band.

25. The implant of claim 24, wherein the implant and the autograft are configured in an orientation selected from the group consisting of the implant being placed around the autograft, the implant being surrounded by the autograft, and the implant being placed alongside the autograft.

26. The implant of claim 1, wherein the biocompatible scaffold further comprises at least one additional biological component applied thereto.

27. The implant of claim 26, wherein the at least one additional biological component comprises growth factors, matrix proteins, peptides, antibodies, enzymes, cytokines, isolated cells, platelets, and combinations thereof.

28. The implant of claim 1, wherein the biocompatible scaffold further comprises an adhesion agent for anchoring the suspension of tissue fragment to the biocompatible scaffold.

29. The implant of claim 28, wherein the adhesion agent comprises an anchoring agent selected from the group consisting of hyaluronic acid, fibrin glue, fibrin clot, collagen gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, synthetic acrylate-based adhesives, platelet rich plasma (PRP), Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

30. The implant of claim 28, wherein the adhesion agent comprises a cross-linking agent selected from the group consisting of divinyl sulfone (DVS), polyethylene glycon divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light, pH, temperature, and combinations thereof.

31. The implant of claim 1, wherein the scaffold has an elliptical shape.

32. The implant of claim 1, wherein the tissue fragments include cells that migrate to the scaffold and proliferate therein.

33. The implant of claim 14, wherein cells migrate from the tissue fragments to the scaffold and proliferate therein.

\* \* \* \* \*